US012806290B2

(12) United States Patent
Madera et al.

(10) Patent No.: US 12,806,290 B2
(45) Date of Patent: Nov. 24, 2026

(54) SYNERGISTIC EFFECT OF SMN1 AND MIR-23A IN TREATING SPINAL MUSCULAR ATROPHY

(71) Applicant: JOINT STOCK COMPANY «BIOCAD», Saint Petersburg (RU)

(72) Inventors: Dmitriy Aleksandrovich Madera, Moscow (RU); Anna Sergeevna Veselova, Saint Petersburg (RU); Aleksei Sergeevich Siutkin, G. Neftekamsk (RU); Pavel Mikhailovich Gershovich, Saint Petersburg (RU); Dmitry Valentinovich Morozov, Saint Petersburg (RU)

( * ) Notice: Subject to any disclaimer, the term of this patent is extended or adjusted under 35 U.S.C. 154(b) by 532 days.

(21) Appl. No.: 18/274,496

(22) PCT Filed: Jan. 28, 2022

(86) PCT No.: PCT/RU2022/000025
§ 371 (c)(1),
(2) Date: Jul. 27, 2023

(87) PCT Pub. No.: WO2022/164351
PCT Pub. Date: Aug. 4, 2022

(65) Prior Publication Data

US 2024/0091383 A1 Mar. 21, 2024

(30) Foreign Application Priority Data

Jan. 29, 2021 (RU) ........................... RU2021102051

(51) Int. Cl.
*C07K 14/47* (2006.01)
*A61K 48/00* (2006.01)
*A61P 21/00* (2006.01)
*C12N 15/86* (2006.01)

(52) U.S. Cl.
CPC .......... *A61K 48/0058* (2013.01); *C12N 15/86* (2013.01); *C12N 2310/141* (2013.01); *C12N 2310/31* (2013.01); *C12N 2750/14143* (2013.01)

(58) Field of Classification Search
CPC .. A61K 48/0058; A61K 48/005; C12N 15/86; C12N 2310/141; C12N 2310/31; C12N 2750/14143; C12N 2830/00; C12N 15/113; C12N 2320/31; C12N 2840/00; C07K 14/47; A61P 21/00
See application file for complete search history.

(56) References Cited

U.S. PATENT DOCUMENTS

| | | | | |
|---|---|---|---|---|
| 8,466,271 B2 * | 6/2013 | Enenkel | C12N 15/67 435/328 |
| 10,738,326 B2 | 8/2020 | Muramatsu | |
| 2013/0224836 A1 * | 8/2013 | Muramatsu | C12N 15/86 435/235.1 |
| 2018/0353624 A1 * | 12/2018 | Wilson | C12N 15/86 |
| 2023/0212609 A1 * | 7/2023 | Madera | C12N 15/86 424/93.2 |

FOREIGN PATENT DOCUMENTS

| | | | | |
|---|---|---|---|---|
| RU | 2742837 C1 * | 2/2021 | C12N 15/86 |
| WO | 2010/129021 A1 | 11/2010 | |
| WO | 2015/060722 A1 | 4/2015 | |
| WO | 2015/158749 A2 | 10/2015 | |
| WO | 2017/066579 A1 | 4/2017 | |
| WO | 2017/106354 A1 | 6/2017 | |
| WO | 2017/136536 A1 | 8/2017 | |

OTHER PUBLICATIONS

Kaifer, Kevin A., et al. "AAV9-mediated delivery of miR-23a reduces disease severity in Smn2B/– SMA model mice." Human molecular genetics 28.19 (2019): 3199-3210. (Year: 2019).*
GenBank, *Homo sapiens* uncharacterized LOC284454 (LOC284454), long non-coding RNA, NR_036515.2, obtained online at: https://www.ncbi.nlm.nih.gov/nuccore/1511202154?sat=48&satkey=92606592, downloaded on Jan. 24, 2026. (Year: 2018).*
International application No. PCT/RU2022/000025 International Search Report dated Jun. 16, 2022.
International application No. PCT/RU2022/000025 Written Opinion of the International Searching Authority dated Jun. 16, 2022.
Lefebvre et al., Identification and Characterization of a Spinal Muscular Atrophy-Determining Gene. Cell, vol. 80, 155-165, Jan. 13, 1995.
Sumner C.J., Therapeutics development for spinal muscular atrophy. NeuroRX vol. 3, pp. 235-245 (2006).
Xie Q. et al. The atomic structure of adeno-associated virus (AAV-2), a vector for human gene therapy. Proc Natl Acad Sci USA, 2002; 99:10405-10410.
High KA et al., "rAAV human trial experience" Methods Mol Biol. 2011; 807:429-57.
Mori, S. et al., 2004, "Two novel adeno-associated viruses from cynomolgus monkey: pseudotyping characterization of capsid protein", Virology, T. 330 (2): 375-83.

(Continued)

*Primary Examiner* — Abigail Vanhorn
(74) *Attorney, Agent, or Firm* — Anglehart et al.

(57) ABSTRACT

The present application relates to the fields of biotechnology, virology, genetics, and molecular biology. More specifically, the present invention relates to an isolated nucleic acid for producing a gene therapy viral product, said isolated nucleic acid comprising a nucleic acid that encodes the SMN1 protein having the amino acid sequence of SEQ ID NO: 1, and a nucleic acid that encodes the microRNA miR-23a, an expression cassette and a vector based thereon, as well as an AAV9-based recombinant virus for expressing the SMN1 gene in target cells, a pharmaceutical composition that includes said recombinant virus, and various uses of the above recombinant virus and the above composition.

18 Claims, 5 Drawing Sheets

Specification includes a Sequence Listing.

(56) References Cited

OTHER PUBLICATIONS

Dominguez E et al. Intravenous scAAV9 delivery of a codon-optimized SMN1 sequence rescues SMA mice.Human Molecular Genetics, vol. 20, Issue 4, Feb. 15, 2011, pp. 681-693, https://doi.org/10.1093/hmg/ddq514.

Sequence Q16637-1. Posted Jan. 11, 1996. online. Retrieved Jul. 18, 2023 from https://www.uniprot.org/uniprotkb/Q16637/entry#Q16637-1.

Henricks et al. The use of combinations of monoclonal antibodies in clinical oncology. Cancer Treat Rev. Dec. 2015;41(10):859-867).

Szymczak et al. Development of 2a peptide-based strategies in the design of multicistronic vectors. Expert Opin. Biol. Ther. 2005;5:627-638).

* cited by examiner

SYNERGISTIC EFFECT OF SMN1 AND MIR-23A IN TREATING SPINAL MUSCULAR ATROPHY

The content of the ASCII text file of the sequence listing named "P2547US00-Sequence_listing_revised_2" which is 30.1 kb in size was created on Aug. 30, 2023 and electronically submitted herewith via EFS-Web is incorporated herein by reference.

FIELD OF THE INVENTION

The present application relates to the fields of biotechnology, virology, genetics, and molecular biology. More specifically, the present invention relates to an isolated nucleic acid for producing a gene therapy viral product, said isolated nucleic acid comprising a nucleic acid that encodes the SMN1 protein (survival motor neuron protein) having the amino acid sequence of SEQ ID NO: 1, and a nucleic acid that encodes the microRNA miR-23a, to an expression cassette and a vector based thereon, as well as to an AAV9 (adeno-associated virus serotype 9)-based recombinant virus for expressing the SMN1 gene in target cells, to a pharmaceutical composition that includes said recombinant virus, and to various uses of the above recombinant virus and the above composition.

BACKGROUND OF THE INVENTION

Spinal muscular atrophy (SMA) relates to the group of neuromuscular diseases and is characterized by predominantly autosomal recessive inheritance pattern. Currently, the term SMA typically refers to the most common form of the disease that develops as a result of mutations and (or) deletions in the SMN1 (survival motor neuron 1) gene located on the long arm of chromosome 5 (5q11.2-q13.3) (Lefebvre et al., Cell (1995) 80:155-165). The disease is accompanied by motor neuron degeneration in the ventral (anterior) horn of the spinal cord, which leads to hypotonia of the proximal muscles responsible for gross motor skills, for example, crawling, walking, neck control, and also to swallowing disorder and breathing disorder (Sumner C. J., NeuroRx (2006) 3:235-245). Consequently, SMA patients present with increased tendencies for respiratory distress and superaddition of intercurrent diseases.

Gene therapy is a promising approach to treating spinal muscular atrophy.

Adeno-associated virus (AAV) vectors are considered effective in CNS gene therapy because they have suitable toxicity and immunogenicity profiles, they may be used in nerve cell transduction, and they are able to mediate long-term expression in the CNS.

Adeno-associated virus (AAV) is a small (20 nm), independent replication-defective, nonenveloped virus. Many different AAV serotypes have been described in human and primates. The adeno-associated virus genome is composed of (+ or −) single-stranded DNA (ssDNA) being about 4,700 nucleotides long. At the ends of a genomic DNA molecule, there are accommodated terminal inverted repeats (ITRs). The genome comprises two open reading frames (ORFs), Rep and Cap, comprising several alternative reading frames encoding various protein products. The rep products are essential for AAV replication, whereas three capsid proteins (VP1, VP2, and VP3), along with other alternative products, are encoded by the Cap gene. VP1, VP2, and VP3 are present at 1:1:10 ratio to form an icosahedral capsid (Xie Q. et al. The atomic structure of adeno-associated virus (AAV-2), a vector for human gene therapy. Proc Natl Acad Sci USA, 2002; 99:10405-10410). During recombinant AAV (rAAV) vector production, an expression cassette flanked by ITR is packaged into an AAV capsid. The genes required for AAV replication are not included in the cassette. Recombinant AAV is considered one of the safest and most widely used viral vectors for in vivo gene transfer. Vectors can infect cells of multiple tissue types to provide strong and sustained transgene expression. They are also non-pathogenic, and have a low immunogenicity profile (High K A et al., "rAAV human trial experience" Methods Mol Biol. 2011; 807:429-57).

International applications WO2017106354 (A1), WO2010129021 (A1), WO2015060722 (A1), WO2017066579 (A1), WO2015158749 (A2) disclose various variants of AAV comprising the SMN1 gene and uses thereof.

DESCRIPTION OF THE INVENTION

The authors of the invention have developed an isolated nucleic acid for producing a gene therapy viral product, said isolated nucleic acid comprising a nucleic acid that encodes the SMN1 protein having the amino acid sequence of SEQ ID NO: 1, and a nucleic acid that encodes the microRNA miR-23a, an expression cassette and a vector based thereon, as well as an AAV9-based recombinant virus for expressing the SMN1 gene in target cells, a pharmaceutical composition that includes said recombinant virus, and various uses of the above recombinant virus and the above composition. The authors of the invention surprisingly found that miR-23a enhances the functional effect of SMN1 in vitro and revealed the synergistic effect of SMN1 and miR-23a in treating SMA in an animal model of the disease

BRIEF DESCRIPTION OF THE INVENTION

In one aspect, the present invention relates to an isolated nucleic acid for producing a gene therapy viral product, said isolated nucleic acid comprising a nucleic acid that encodes the SMN1 protein (survival motor neuron protein) having the amino acid sequence of SEQ ID NO: 1, and a nucleic acid that encodes the microRNA miR-23a.

In some embodiments, the isolated nucleic acid that encodes the SMN1 protein having the amino acid sequence of SEQ ID NO: 1 includes the nucleotide sequence of SEQ ID NO: 2.

In some embodiments, the isolated nucleic acid includes the microRNA miR-23a that has the nucleotide sequence of SEQ ID NO: 3.

In some embodiments, the isolated nucleic acid includes a nucleic acid encoding the microRNA miR-23a that includes the nucleotide sequence of SEQ ID NO: 4.

In some embodiments, the isolated nucleic acid includes the following elements in the 5'-end to 3'-end direction:

- a nucleic acid that encodes the SMN1 protein having the amino acid sequence of SEQ ID NO: 1, and
- a nucleic acid that encodes the microRNA miR-23a.

In one aspect, the present invention relates to an expression cassette comprising any of the above nucleic acids.

In some embodiments, the expression cassette includes the following elements in the 5'-end to 3'-end direction:

- a left-hand (first) ITR (inverted terminal repeats);
- a CMV (cytomegalovirus) enhancer;
- a CMV (cytomegalovirus) promoter;
- an intron of the hBG1 gene (hemoglobin subunit gamma 1 gene);

a nucleic acid that encodes the SMN1 protein;
an hGH1 polyadenylation signal (human growth hormone gene polyadenylation signal);
an SV40 promoter (simian virus 40 promoter);
a nucleic acid that encodes the microRNA miR-23a;
an SV40 polyadenylation signal (simian virus 40 polyadenylation signal), and
a right-hand (second) ITR.

In some embodiments, the expression cassette includes a nucleic acid with SEQ ID NO: 6.

In one aspect, the present invention relates to an expression vector that includes any of the above nucleic acids or any of the above cassettes.

In one aspect, the present invention relates to an AAV9 (adeno-associated virus serotype 9)-based recombinant virus for the expression of the SMN1 gene in target cells, which includes a capsid and any of the above expression cassettes.

In some embodiments, the AAV9-based recombinant virus includes the AAV9 protein VP1.

In some embodiments, the AAV9-based recombinant virus includes the AAV9 protein VP1 having the amino acid sequence of SEQ ID NO: 7.

In some embodiments, the AAV9-based recombinant virus includes the AAV9 protein VP1 having the amino acid sequence of SEQ ID NO: 7 with one or more point mutations.

In some embodiments, the AAV9-based recombinant virus includes the AAV9 protein VP1 having the amino acid sequence of SEQ ID NO: 7 or the amino acid sequence of SEQ ID NO: 7 with one or more point mutations, and the expression cassette includes the following elements in the 5'-end to 3'-end direction:

a left-hand (first) ITR (inverted terminal repeats);
a CMV (cytomegalovirus) enhancer;
a CMV (cytomegalovirus) promoter;
an intron of the hBG1 gene (hemoglobin subunit gamma 1 gene);
a nucleic acid that encodes the SMN1 protein;
an hGH1 polyadenylation signal (human growth hormone gene polyadenylation signal);
an SV40 promoter (simian virus 40 promoter);
a nucleic acid that encodes the microRNA miR-23a;
an SV40 polyadenylation signal (simian virus 40 polyadenylation signal), and
a right-hand (second) ITR.

In some embodiments, the AAV9-based recombinant virus includes the AAV9 protein VP1 having the amino acid sequence of SEQ ID NO: 7 or the amino acid sequence of SEQ ID NO: 7 with one or more point mutations, and the expression cassette comprises a nucleic acid with SEQ ID NO: 6.

In one aspect, the present invention relates to a pharmaceutical composition for delivering the SMN1 gene to target cells, which includes any of the above AAV9-based recombinant viruses in combination with one or more pharmaceutically acceptable excipients.

In one aspect, the present invention relates to the use of any of the above AAV9-based recombinant viruses or the above composition to deliver the SMN1 gene to target cells.

In one aspect, the present invention relates to the use of any of the above AAV9-based recombinant viruses or the above composition for survival of a subject that has spinal muscular atrophy and/or that does not have fully functional copies of the SMN1 gene.

In one aspect, the present invention relates to the use of any of the above AAV9-based recombinant viruses or the above composition for providing the SMN1 protein to a subject that has spinal muscular atrophy and/or that does not have fully functional copies of the SMN1 gene.

In one aspect, the present invention relates to the use of any of the above AAV9-based recombinant viruses or the above composition for treating spinal muscular atrophy in a subject that has spinal muscular atrophy.

In one aspect, the present invention relates to a method for modulating motor function in a subject having a motor neuron disorder, said method comprising administering a therapeutically effective amount of any of the above AAV9-based recombinant viruses or the above composition into the cells of the subject.

In one aspect, the present invention relates to a method for providing the SMN protein to a subject having spinal muscular atrophy, said method comprising administering a therapeutically effective amount of any of the above AAV9-based recombinant viruses or the above composition into the cells of the subject in need thereof.

In one aspect, the present invention relates to a method for delivering the SMN1 gene to the target cells of a subject having spinal muscular atrophy, said method comprising administering any of the above AAV9-based recombinant viruses or the above composition into the cells of the subject.

In one aspect, the present invention relates to a method for treating spinal muscular atrophy in a subject, said method comprising administering a therapeutically effective amount of any of the above AAV9-based recombinant viruses or the above composition into a subject having spinal muscular atrophy.

For FIGS. 1 to 4:

siNEG is a negative control of siRNA, siSMN1 is siRNA for SMN1.

Figure 1:
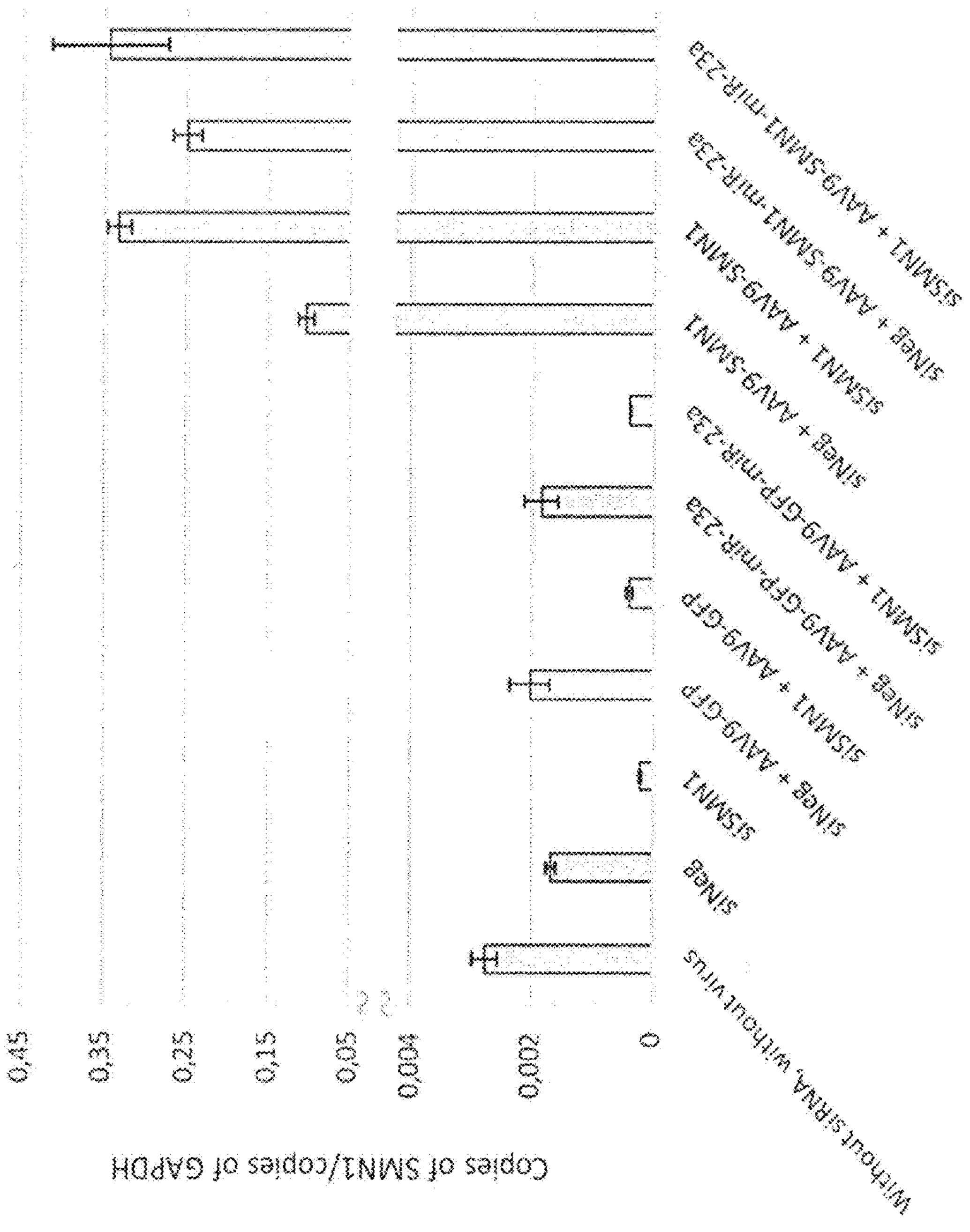
FIG. 1 is a graph showing SMN1 expression at mRNA level following SMN1 knockdown using siRNA and transduction by AAV9-GFP, AAV9-GFP-miR-23a, AAV9-SMN1 and AAV9-SMN1-miR-23a viruses. U-87 cells were transfected with 20 nmol/l siRNA specific for SMN1 (or control siRNA), thereafter they were transduced by the viruses AAV9-GFP, AAV9-GFP-miR-23a, AAV9-SMN1 and AAV9-SMN1-miR-23a at MOI=400,000. 120 h following transduction, the copy number of the SMN1 gene in each sample was determined by quantitative PCR (n=3). The copy number of the GAPDH household gene was also determined. All obtained levels for SMN1 were normalized to the amounts of copies of the GAPDH gene in each sample. Provided are data on normalized mean copy number of SMN1, showing standard deviation.
Figure 2:
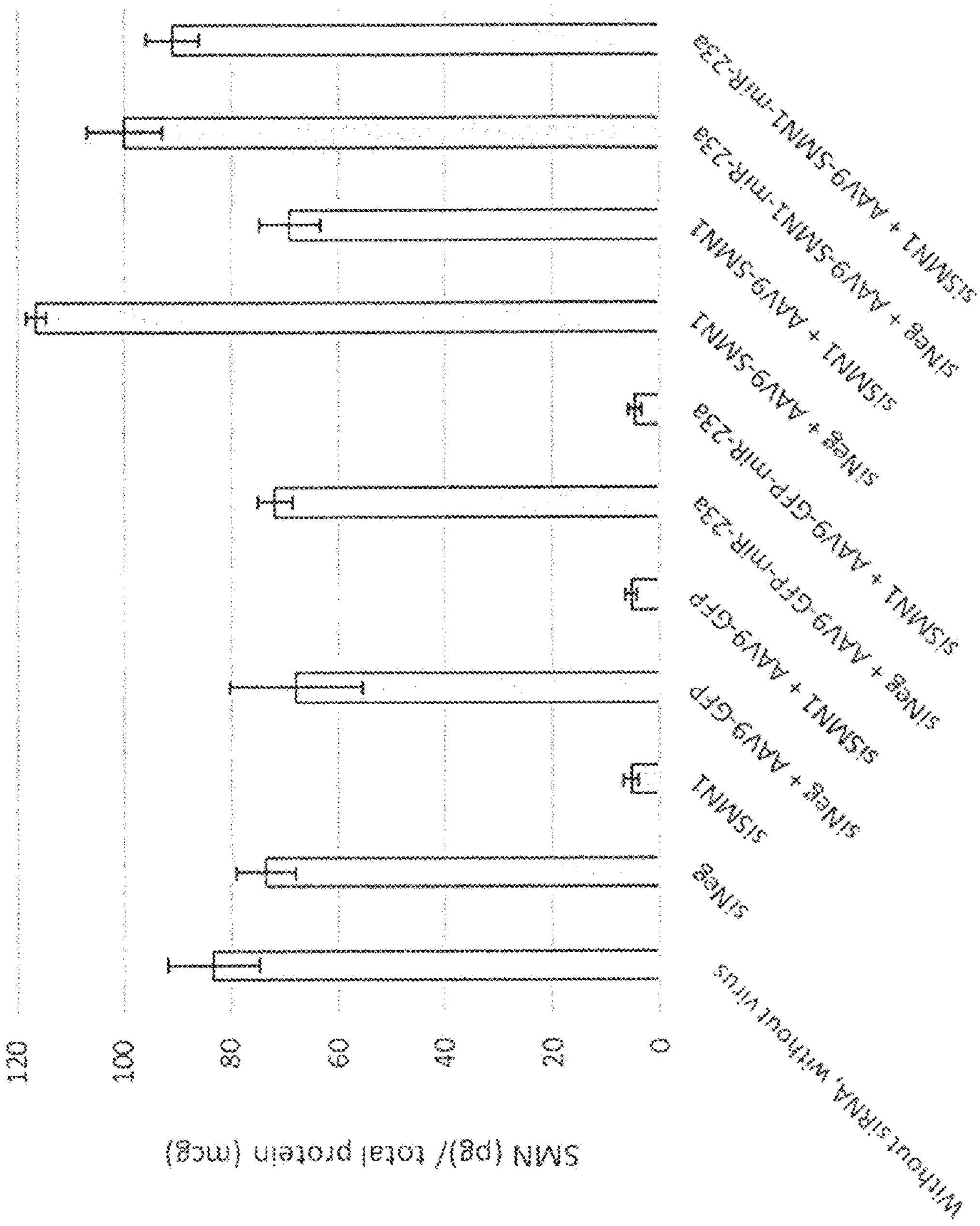
FIG. 2 is a graph showing SMN expression at protein level following SMN1 knockdown using siRNA and transduction by the viruses AAV9-GFP, AAV9-GFP-miR-23a, AAV9-SMN1 and AAV9-SMN1-miR-23a. U-87 cells were transfected with 20 nmol/l siRNA specific for SMN1 (or control siRNA), thereafter they were transduced by the viruses AAV9-GFP, AAV9-GFP-miR-23a, AAV9-SMN1 and AAV9-SMN1-miR-23a at MOI=400,000. 120 h following transduction, the amount of SMN protein in each sample was determined using ELISA (n=3). All resulting amounts of SMN protein (in pg) were normalized against the total amount of protein in each sample (in μg). Provided are data on normalized mean amount of SMN protein, showing standard deviation.
Figure 3:
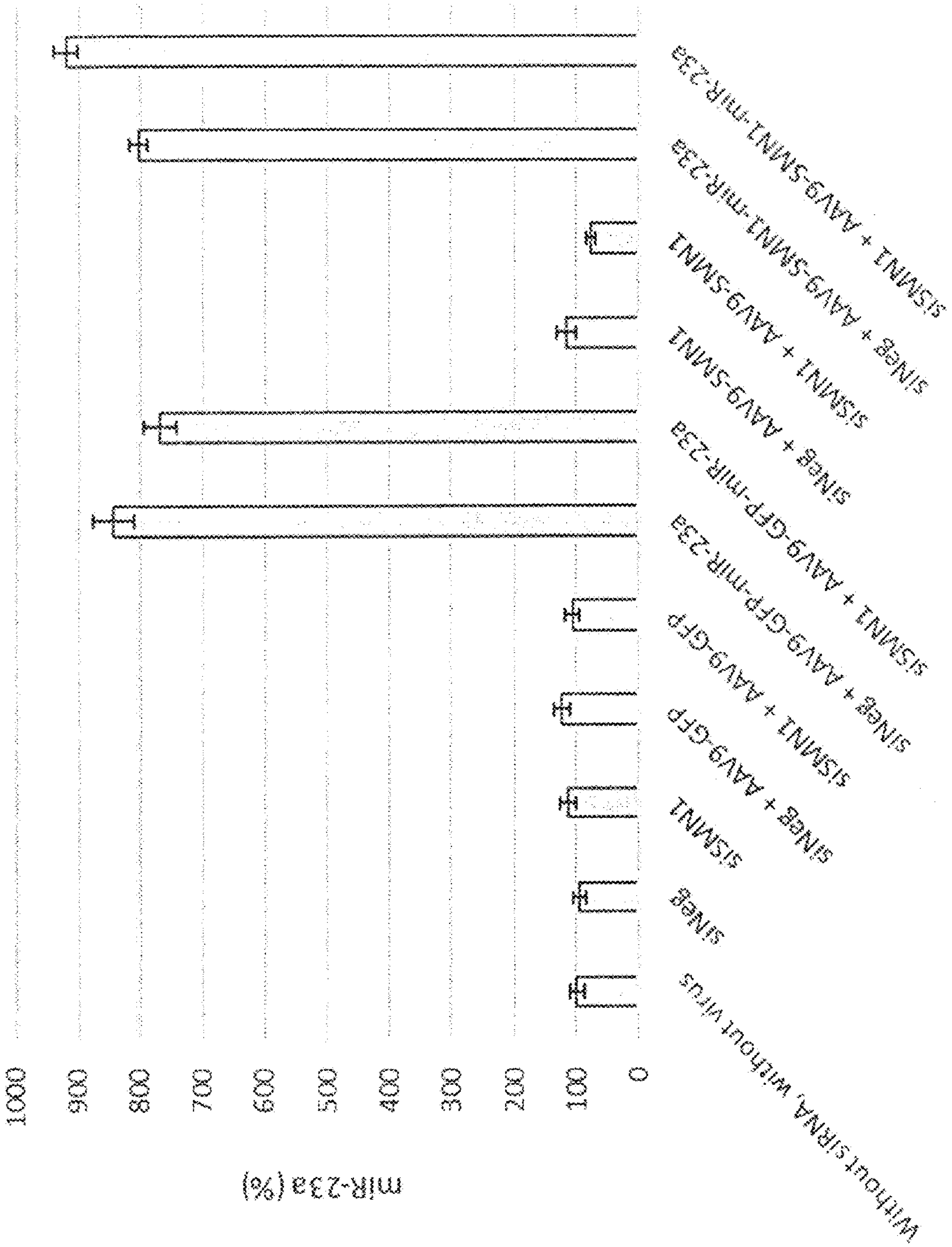
FIG. 3 is a graph showing miR-23a expression following SMN1 knockdown using siRNA and transduction by the viruses AAV9-GFP, AAV9-GFP-miR-23a, AAV9-SMN1 and AAV9-SMN1-miR-23a. U-87 cells were transfected with 20 nmol/l siRNA specific for SMN1 (or control siRNA), thereafter they were transduced by the viruses AAV9-GFP, AAV9-GFP-miR-23a, AAV9-SMN1 and AAV9-SMN1-miR-23a at MOI=400,000. 120 h following transduction, the amount of miR-23a against the copy number of the GAPDH gene in each sample was determined by quantitative PCR (n=3), using the MET method. Provided are data on normalized mean amount of miR-23a, showing standard deviation. The relative amount of miR-23a in non-transfected and non-transduced controls was taken as 100%.
Figure 4:
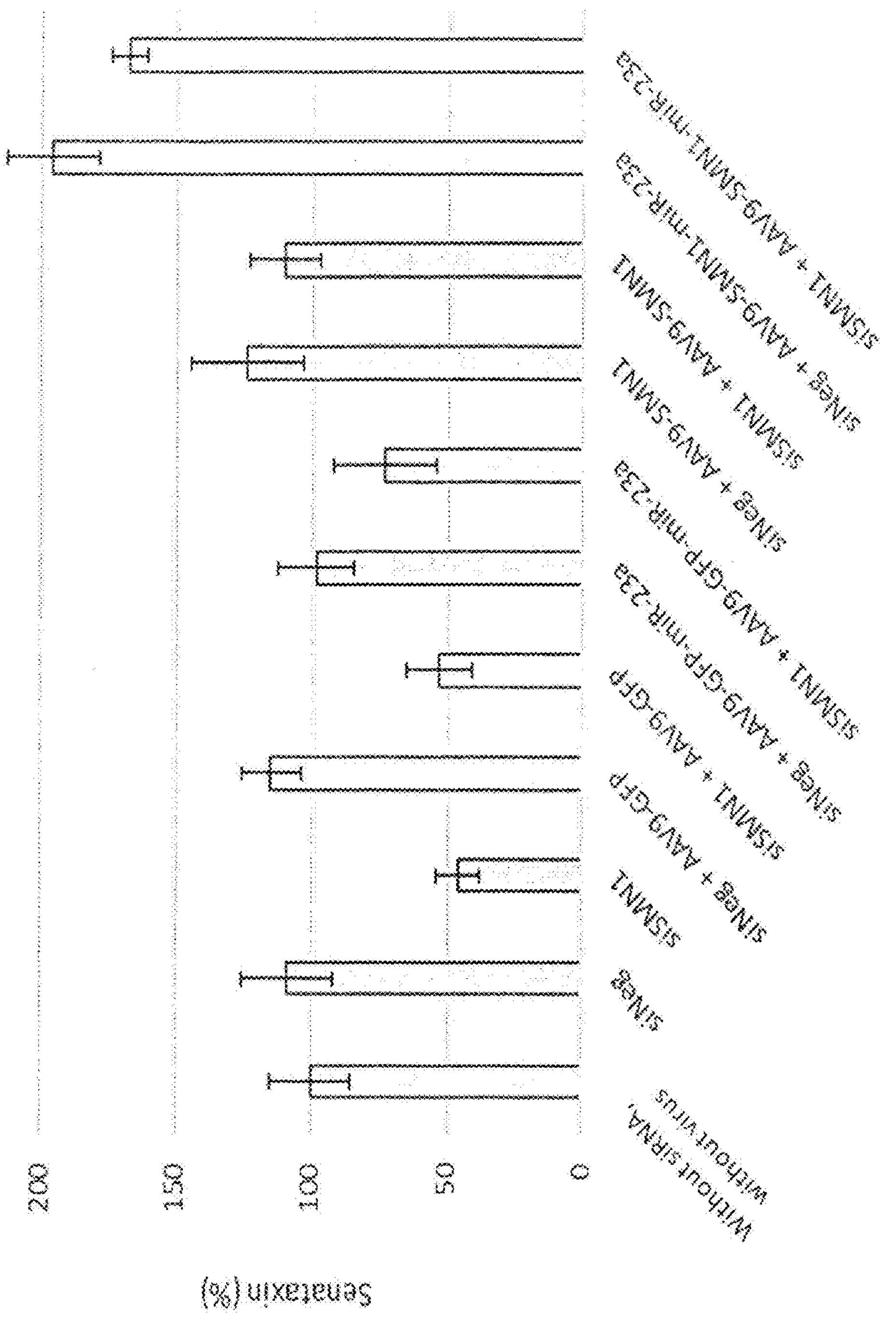
FIG. 4 is a graph showing Senataxin expression following SMN1 knockdown using siRNA and transduction by the viruses AAV9-GFP, AAV9-GFP-miR-23a, AAV9-SMN1 and AAV9-SMN1-miR-23a. U-87 cells were transfected with 20 nmol/l siRNA specific for wild-type SMN1 (or control siRNA), thereafter they were transduced by the viruses AAV9-GFP, AAV9-GFP-miR-23a, AAV9-SMN1 and AAV9-SMN1-miR-23a at MOI=400,000. 120 h following transduction, the amount of Senataxin against that of Vinculin protein in each sample was determined using Western blot. Provided is a graph showing normalized expression of Senataxin against Vinculin in experimental samples with indication of standard deviations (n=3). The relative amount of Senataxin in non-transfected and non-transduced controls was taken as 100%.
Figure 5:
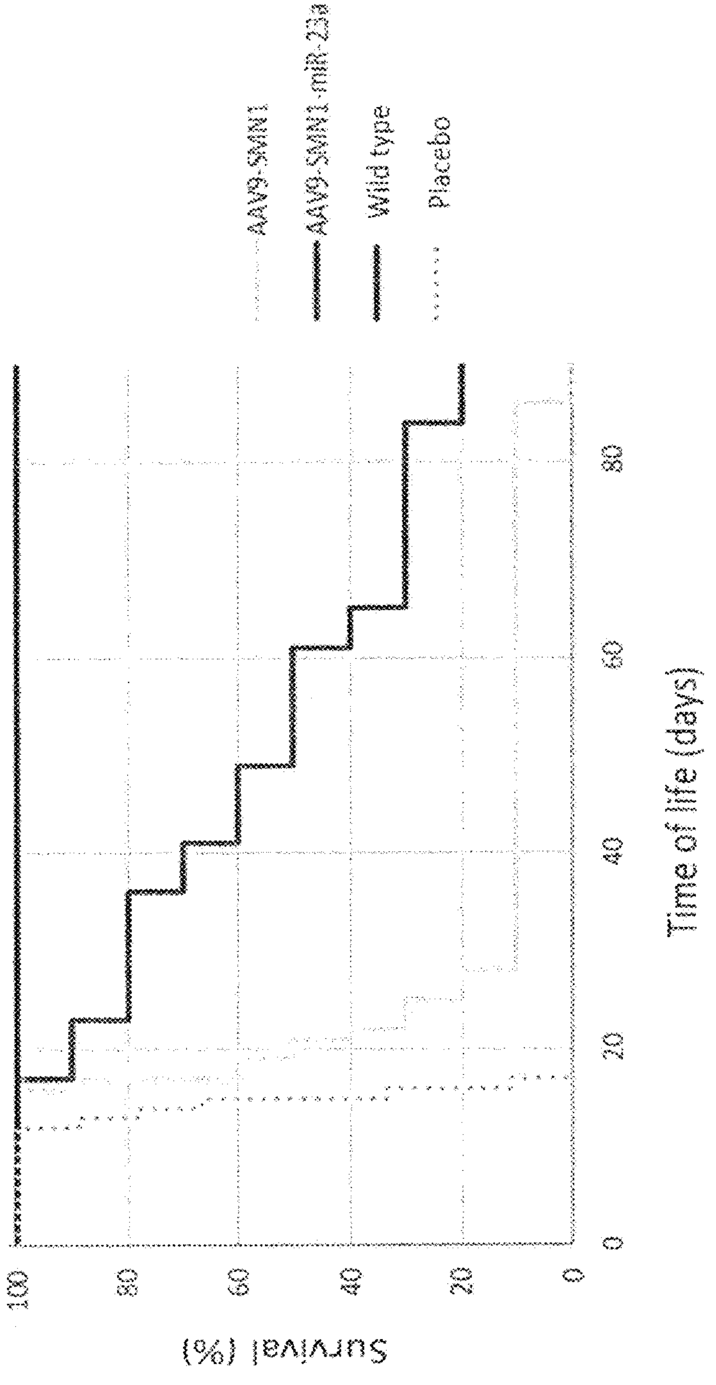

FIG. 5 is a graph showing the survival curves for SMA model mice injected with the viruses AAV9-SMN1 and AAV9-SMN1-miR-23a. Survival curves for placebo-injected animals and wild-type control mice (from the same litter as the experimental ones) are also shown.

DEFINITIONS AND GENERAL METHODS

Unless defined otherwise herein, all technical and scientific terms used in connection with the present invention will have the same meaning as is commonly understood by those skilled in the art.

Furthermore, unless otherwise required by context, singular terms shall include plural terms, and the plural terms shall include the singular terms. Typically, the present classification and methods of cell culture, molecular biology, immunology, microbiology, genetics, analytical chemistry, organic synthesis chemistry, medical and pharmaceutical chemistry, as well as hybridization and chemistry of protein and nucleic acids described herein are well known by those skilled and widely used in the art. Enzyme reactions and purification methods are performed according to the manufacturer's guidelines, as is common in the art, or as described herein.

"Isolated" means altered or removed from the natural state. For example, a nucleic acid or a peptide naturally present in an animal is not "isolated", but the same nucleic acid or peptide partially or completely separated from the coexisting materials of its natural state is "isolated". An isolated nucleic acid or protein can exist in substantially purified form, or can exist in a non-native environment such as, for example, a genetically modified cell.

The terms "naturally occurring," "native," or "wild-type" are used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

The term "genome" refers to the complete genetic material of an organism.

As used in the present description and claims that follow, unless otherwise dictated by the context, the words "include" and "comprise," or variations thereof such as "having," "includes", "including", "comprises," or "comprising," will be understood to imply the inclusion of a stated integer or group of integers but not the exclusion of any other integer or group of integers.

Protein (Peptide)

As used in the present description, the terms "peptide", "polypeptide" and "protein" are used interchangeably, and they refer to a compound consisting of amino acid residues that are covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used in the present description, the term refers to both short chains, which also commonly are referred to in the art, for example, as peptides, oligopeptides and oligomers, and to longer chains, which generally are referred to in the art as proteins, of which there are many types. "Polypeptides" include, inter alia, for example, biologically active fragments, substantially homologous polypeptides, oligopeptides, homodimers, heterodimers, variants of polypeptides, modified polypeptides, derivatives, analogs, fusion proteins. The polypeptides include natural peptides, recombinant peptides, synthetic peptides, or a combination thereof.

Nucleic Acid Molecules

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, determining a fragment or a region of a nucleic acid, containing unnatural nucleotides or not, and being either a double-strand DNA or RNA, a single-strand DNA or RNA, or transcription products of said DNAs.

As used in the present description, polynucleotides include, as non-limiting examples, all nucleic acid sequences which are obtained by any means available in the art, including, as non-limiting examples, recombinant means, i.e. the cloning of nucleic acid sequences from a recombinant library or a cell genome, using ordinary cloning technology and PCR and the like, and by synthetic means.

It should also be included here that the present invention does not relate to nucleotide sequences in their natural chromosomal environment, i.e. in a natural state. The sequences of the present invention have been isolated and/or purified, i.e., they were sampled directly or indirectly, for example by copying, their environment having been at least partially modified. Thus, isolated nucleic acids obtained by recombinant genetics, by means, for example, of host cells, or obtained by chemical synthesis should also be mentioned here.

Unless otherwise indicated, the term nucleotide sequence encompasses its complement. Thus, a nucleic acid having a particular sequence should be understood as one which encompasses the complementary strand thereof with the complementary sequence thereof.

Adeno-Associated Virus (AAV)

Viruses of the Parvoviridae family are small DNA-containing animal viruses. The Parvoviridae family may be divided into two subfamilies: the Parvovirinae, which members infect vertebrates, and the Densovirinae, which members infect insects. By 2006, there have been 11 serotypes of adeno-associated virus described (Mori, S. ET AL., 2004, "Two novel adeno-associated viruses from cynomolgus monkey: pseudotyping characterization of capsid protein", Virology, T. 330 (2): 375-83). All of the known serotypes can infect cells from multiple tissue types. Tissue specificity is determined by the capsid protein serotype; therefore, the adeno-associated virus-based vectors are constructed by assigning the desired serotype. Further information on parvoviruses and other members of the Parvoviridae is described in the literature (Kenneth I. Berns, "Parvoviridae: The Viruses and Their Replication", Chapter 69 in Fields Virology (3d Ed. 1996)).

The genomic organization of all known AAV serotypes is very similar. The genome of AAV is a linear, single-stranded DNA molecule that is less than about 5000 nucleotides (nt) in length. Inverted terminal repeats (ITRs) flank the unique coding nucleotide sequences of replication of non-structural proteins (Rep) and structural proteins (Cap). The Cap gene encodes the VP proteins (VP1, VP2, and VP3) which form the capsid. The terminal 145 nucleotides are self-complementary and are organized such that an energetically stable intramolecular duplex forming a T-shaped hairpin may be formed. Such hairpin structures function as an origin for virus DNA replication, serving as primers for the cellular DNA polymerase complex. Following wild-type AAV (wtAAV) infection in mammalian cells, the Rep genes (e.g. Rep78 and Rep52) are expressed using the P5 promoter and the P19 promoter, respectively, and the both Rep proteins have a certain function in the replication of the viral genome. A splicing event in the Rep open reading frame (Rep ORF) results in the expression of actually four Rep proteins (e.g. Rep78, Rep68, Rep52, and Rep40). However, it has been shown that the unspliced mRNA encoding Rep78 and Rep52 proteins is sufficient for AAV vector production in mammalian cells.

Vector

The term "vector" as used herein means a nucleic acid molecule capable of transporting another nucleic acid to which it has been linked. Furthermore, the term "vector" herein refers to a viral particle capable of transporting a nucleic acid.

As used in the present description, the term "expression" is defined as the transcription and/or translation of a particular nucleotide sequence driven by its promoter.

Use

"Gene therapy" is the insertion of genes into subject's cells and/or tissues to treat a disease, typically hereditary diseases, in which a defective mutant allele is replaced with a functional one.

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of a disease, disorder, or condition. Further, references herein to "treatment" include references to curative, palliative and prophylactic treatment.

In one aspect, the subject of treatment, or patient, is a mammal, preferably a human subject. Said subject may be either male or female, of any age.

The term "disorder" means any condition that would benefit from treatment with the compound of the present invention.

"Disease" is a state of health of a subject where the subject cannot maintain homeostasis, and where if the disease is not ameliorated then the subject's health continues to deteriorate.

The terms "subject," "patient," "individual," and the like are used interchangeably in the present description, and they refer to any animal which is amenable to the methods described in the present description. In certain non-limiting embodiments, the subject, patient or individual is a human. Said subject may be either male or female, of any age.

"Therapeutically effective amount" or "effective amount" refers to that amount of the therapeutic agent being administered which will relieve to some extent one or more of the symptoms of the disease being treated.

Detailed Description of the Invention

Nucleic Acid

In one aspect, the present invention relates to an isolated nucleic acid for producing a gene therapy viral product, said isolated nucleic acid comprising a nucleic acid that encodes the SMN1 protein (survival motor neuron protein) having the amino acid sequence

```
                                          (SEQ ID NO: 1)
MAMSSGGSGGGVPEQEDSVLFRRGTGQSDDSDIWDDTALIKAYDKAVAS

FKHALKNGDICETSGKPKTTPKRKPAKKNKSQKKNTAASLQQWKVGDKC

SAIWSEDGCIYPATIASIDFKRETCVVVYTGYGNREEQNLSDLLSPICE

VANNIEQNAQENENESQVSTDESENSRSPGNKSDNIKPKSAPWNSFLPP

PPPMPGPRLGPGKPGLKFNGPPPPPPPPPPPHLLSCWLPPFPSGPPIIPP

PPPICPDSLDDADALGSMLISWYMSGYHTGYYMGFRQNQKEGRCSHSL

N,
```

and a nucleic acid that encodes the microRNA miR-23a;

In some embodiments, the above nucleic acid is used for producing a gene therapy viral product that is an expression vector of the invention or an AAV9-based recombinant virus of the invention.

An "isolated" nucleic acid molecule is one which is identified and separated from at least one nucleic acid molecule-impurity, which the former is typically bound to in the natural source of nuclease nucleic acid. An isolated nucleic acid molecule is different from the form or set in which it is found under natural conditions. Thus, an isolated nucleic acid molecule is different from a nucleic acid molecule that exists in cells under natural conditions.

In some embodiments, the isolated nucleic acid is DNA.

As would be appreciated by those skilled in the art, because of the redundancy of the genetic code, a variety of different DNA sequences can encode the SMN1 protein having the amino acid sequence of SEQ ID NO: 1. It is well within the skill of a person trained in the art to create these alternative DNA sequences encoding the same amino acid sequences. Such variant DNA sequences are within the scope of the present invention.

In some embodiments, the isolated nucleic acid that encodes the SMN1 protein having the amino acid sequence of SEQ ID NO: 1 includes the nucleotide sequence

```
                                        (SEQ ID NO: 2)
ATGGCCATGAGCAGCGGCGGCAGCGGCGGCGGCGTGCCTGAGCAAGAGG

ACAGCGTGCTGTTCAGAAGAGGCACCGGCCAGAGCGACGACAGCGACAT

CTGGGACGACACCGCCCTGATCAAGGCCTACGACAAGGCCGTGGCCAGC

TTCAAGCACGCCCTGAAGAACGGCGACATCTGCGAGACCAGCGGCAAGC

CCAAGACCACCCCCAAGAGAAAGCCCGCCAAGAAGAACAAGAGCCAGAA

GAAGAACACCGCCGCCAGCCTGCAGCAGTGGAAGGTGGGCGACAAGTGC

AGCGCCATCTGGAGCGAGGACGGCTGCATCTACCCCGCCACCATCGCCA

GCATCGACTTCAAGAGAGAGACCTGCGTGGTGGTGTACACCGGCTACGG

CAACAGAGAGGAGCAGAACCTGAGCGACCTGCTGAGCCCCATCTGCGAG

GTGGCCAACAACATCGAGCAGAACGCCCAAGAGAACGAGAACGAGAGCC

AAGTGAGCACCGACGAGAGCGAGAACAGCAGAAGCCCCGGCAACAAGAG

CGACAACATCAAGCCCAAGAGCGCCCCCTGGAACAGCTTCCTGCCCCCT

CCCCCCCCTATGCCCGGCCCTAGACTGGGCCCTGGCAAGCCTGGCCTGA

AGTTCAACGGCCCCCCCCCCCCTCCTCCTCCTCCTCCTCCTCACCTGCT

GAGCTGCTGGCTGCCCCCCTTCCCCAGCGGCCCTCCTATCATCCCTCCT

CCCCCCCCCATCTGCCCCGACAGCCTGGACGACGCCGACGCCCTGGGCA

GCATGCTGATCAGCTGGTACATGAGCGGCTACCACACCGGCTACTACAT

GGGCTTCAGACAGAACCAGAAGGAGGGCCGGTGCAGCCACAGCCTGAA

C.
```

In some embodiments, the isolated nucleic acid includes the microRNA miR-23a that has the nucleotide sequence

```
                                        (SEQ ID NO: 3)
GGCCGGCUGGGGUUCCUGGGGAUGGGAUUUGCUUCCUGUCACAAAUCAC
AUUGCCAGGGAUUUCCAACCGACC.
```

In some embodiments, the isolated nucleic acid includes a nucleic acid encoding the microRNA miR-23a that includes the nucleotide sequence

```
                                        (SEQ ID NO: 4)
CATGCAAGTTGCTGTAGCCTCCTTGTCCCGCATGGGCCCTCTAGGTATC

TCTGCCTCTCCAGTCCTGGGGCTGGAACGGAGGGCACAGCTAGGCTCCA

GCTCCCCGTGTGGTGGCTCCTGCATATGAGAAAAGAGCTTCCCTGTGAT

CAAAGGAAGCATCTGGGGACCTGGAGGGGAGGTGTCCCCAAATCTCATT

ACCTCCTTTGCTCTCTCTCTCTTTCTCCCCTCCAGGTGCCAGCCTCTGG

CCCCGCCCGGTGCCCCCCTCACCCCTGTGCCACGGCCGGCTGGGGTTCC

TGGGGATGGGATTTGCTTCCTGTCACAAATCACATTGCCAGGGATTTCC

AACCGACCCTGAGCTCTGCCACCGAGGATGCTGCCCGGGGACGGGGTGG

CAGAGAGGCCCCGAAGCCTGTGCCTGGCCTGAGGAGCAGGGCTTAGCTG

CTTGTGAGCAGGGTCCACACCAAGTCGTGTTCACAGTGGCTAAGTTCCG

CCCCCCAGGCCCTCACCTCCTCTGGCCTTGCCGCCTGTCCCCTGCTGCC
```

-continued

```
GCCTGTCTGCCTGCCATCCTGCTGCCTGGCCTCCCTGGGCTCTGCCTCC

CGTGCCTACTGAGCTGAAACACAGTTGGTTTGTGTACACTGGCTCAGTT

CAGCAGGAACA.
```

The above nucleic acid, which encodes the microRNA miR-23a, having the nucleotide sequence SEQ ID NO: 4 is a nucleic acid before processing.

Following processing, the nucleic acid, which encodes the microRNA miR-23a, has the nucleotide sequence

```
                                        (SEQ ID NO: 5)
GGCCGGCTGGGGTTCCTGGGGATGGGATTTGCTTCCTGTCACAAATCAC
ATTGCCAGGGATTTCCAACCGACC.
```

In some embodiments, the isolated nucleic acid includes the following elements in the 5'-end to 3'-end direction:

- a nucleic acid that encodes the SMN1 protein having the amino acid sequence of SEQ ID NO: 1, and
- a nucleic acid that encodes the microRNA miR-23a.

Expression Cassette. Expression Vector.

In one aspect, the present invention relates to an expression cassette comprising any of the above nucleic acids.

The term "expression cassette", as used herein, refers in particular to a DNA fragment that is capable, in an appropriate setting, of triggering the expression of a polynucleotide encoding a polypeptide of interest that is included in said expression cassette. When introduced into a host cell, the expression cassette is, inter alia, capable of engaging cellular mechanisms to transcribe the polynucleotide encoding the polypeptide of interest into RNA that is then typically further processed and eventually translated into the polypeptide of interest. The expression cassette may be contained in an expression vector.

The term "cassette which expresses" or "expression cassette", as used herein, refers in particular to a DNA fragment that is capable, in an appropriate setting, of triggering the expression of a polynucleotide encoding a polypeptide of interest that is included in said expression cassette. When introduced into a host cell, the expression cassette is, inter alia, capable of engaging cellular mechanisms to transcribe the polynucleotide encoding the polypeptide of interest into RNA that is then typically further processed and eventually translated into the polypeptide of interest. The expression cassette may be contained in an expression vector.

The expression cassette of the present invention comprises a promoter as an element. The term "promoter" as used herein refers in particular to a DNA element that promotes the transcription of a polynucleotide to which the promoter is operably linked. The promoter may further form part of a promoter/enhancer element. Although the physical boundaries between the "promoter" and "enhancer" elements are not always clear, the term "promoter" typically refers to a site on the nucleic acid molecule to which an RNA polymerase and/or any associated factors binds and at which transcription is initiated. Enhancers potentiate promoter activity temporally as well as spatially. Many promoters are known in the art to be transcriptionally active in a wide range of cell types. Promoters can be divided into two classes, those that function constitutively and those that are regulated by induction or derepression. The both classes are suitable for protein expression. Promoters that are used for high-level production of polypeptides in eukaryotic cells and, in particular, in mammalian cells, should be strong and preferably active in a wide range of cell types. Strong constitutive promoters which are capable of driving expression in many cell types are well known in the art and, therefore, it is not herein necessary to describe them in detail. In accordance with the idea of the present invention, it is preferable to use the cytomegalovirus (CMV) promoter. A promoter or promoter/enhancer derived from the immediate early (IE) region of human cytomegalovirus (hCMV) is particularly suitable as a promoter in the expression cassette of the present invention. Human cytomegalovirus (hCMV) immediate early (IE) region and functional expression-inducing and/or functional expression-enhancing fragments derived therefrom, for example, have been disclosed in EP0173177 and EP0323997, and are well known in the art. Thus, several fragments of the hCMV immediate early (IE) region may be used as a promoter and/or promoter/enhancer. According to one embodiment of the invention, the human CMV promoter is used in the expression cassette of the present invention.

In some embodiments, the expression cassette includes the following elements in the 5'-end to 3'-end direction:

- a left-hand (first) ITR (inverted terminal repeats);
- a CMV (cytomegalovirus) enhancer;
- a CMV (cytomegalovirus) promoter;
- an intron of the hBG1 gene (hemoglobin subunit gamma 1 gene);
- a nucleic acid that encodes the SMN1 protein;
- an hGH1 polyadenylation signal (human growth hormone gene polyadenylation signal);
- an SV40 promoter (simian virus 40 promoter);
- a nucleic acid that encodes the microRNA miR-23a;
- an SV40 polyadenylation signal (simian virus 40 polyadenylation signal), and
- a right-hand (second) ITR.

In some embodiments, the left-hand (first) ITR (inverted terminal repeats) has the following nucleic acid sequence:

(SEQ ID NO: 10)

```
cctgcaggcagctgcgcgctcgctcgctcactgaggccgcccgggcgtc
gggcgacctttggtcgcccggcctcagtgagcgagcgagcgcgcagaga
gggagtggccaactccatcactaggggttcct.
```

In some embodiments, the CMV (cytomegalovirus) enhancer has the following nucleic acid sequence:

(SEQ ID NO: 11)

```
cgttacataacttacggtaaatggcccgcctggctgaccgcccaacgac
ccccgcccattgacgtcaataatgacgtatgttcccatagtaacgCcaa
tagggactttccattgacgtcaatgggtggagtatttacggtaaactgc
ccacttggcagtacatcaagtgtatcatatgccaagtacgccccctatt
gacgtcaatgacggtaaatggcccgcctggcattatgcccagtacatga
ccttatgggactttcctacttggcagtacatctacgtattagtcatcgc
tattaccatg
```

In some embodiments, the CMV (cytomegalovirus) promoter has the following nucleic acid sequence:

(SEQ ID NO: 12)

```
gtgatgcggttttggcagtacatcaatgggcgtggatagcggtttgact
cacggggatttccaagtctccaccccattgacgtcaatgggagtttgtt
ttgGcaccaaaatcaacgggactttccaaaatgtcgtaacaactccgcc
```

-continued

```
ccattgacgcaaatgggcggtaggcgtgtacggtgggaggtctatataa
gcagagct.
```

In some embodiments, the intron of the hBG1 (hemoglobin subunit gamma 1) gene has the following nucleic acid sequence:

(SEQ ID NO: 13)

```
cgaatcccggccgggaacggtgcattggaacgcggattccccgtgccaa
gagtgacgtaagtaccgcctatagagtctataggcccacaaaaaatgct
ttcttcttttaatatacttttttgtttatcttatttctaatactttccc
taatctctttctttcagggcaataatgatacaatgtatcatgcctcttt
gcaccattctaaagaataacagtgataatttctgggttaaggcaatagc
aatatttctgcatataaatatttctgcatataaattgtaactgatgtaa
gaggtttcatattgctaatagcagctacaatccagctaccattctgctt
ttattttatggttgggataaggctggattattctgagtccaagctaggc
ccttttgctaatcatgttcatacctcttatcttcctcccacagctcctg
ggcaacgtgctggtctgtgtgctggcccatcactttggcaaagaattgg
gat.
```

In some embodiments, the hGH1 (human growth hormone 1 gene) polyadenylation signal has the following nucleic acid sequence:

(SEQ ID NO: 14)

```
acgggtggcatccctgtgacccctccccagtgcctctcctggccctgga
agttgccactccagtgcccaccagccttgtcctaataaaattaagttgc
atcattttgtctgactaggtgtccttctataatattatggggtggaggg
gggtggtatggagcaaggggcaagttgggaagacaacctgtagggcctg
cggggtctattgggaaccaagctggagtgcagtggcacaatcttggctc
actgcaatctccgcctcctgggttcaagcgattctcctgcctcagcctc
ccgagttgttgggattccaggcatgcatgaccaggctcagctaattttt
gtttttttggtagagacggggtttcaccatattggccaggctggtctcc
aactcctaatctcaggtgatctacccaccttggcctcccaaattgctgg
gattacaggcgtgaaccactgctcccttccctgtcctt.
```

In some embodiments, the SV40 promoter (simian virus 40 promoter) has the following nucleic acid sequence:

(SEQ ID NO: 15)

```
TGCATCTCAATTAGTCAGCAACCATAGtcccgcccctaactccgcccat
cccgcccctaactccgcccagttccgcccattctccgccccatcgctga
ctaattttttttatttatgcagaggccgaggccgcctcggcctctgagc
tattccagaagtagtgaggaggcttttttggaggcctaggcttttgcaa
aaagct.
```

In some embodiments, the SV40 polyadenylation signal (simian virus 40 polyadenylation signal) has the following nucleic acid sequence:

(SEQ ID NO: 16)
aataaaatatctttattttcattacatctgtgtgttggttttttgtgtg aatcgatagtactaacatacgctctccatcaaaacaaaacgaaacaaaa caaactagcaaaataggctgtccccagtgcaaGTGCAGGTGCCAGAACA

TTTCTCT.

In some embodiments, the right-hand (second) ITR has the following nucleic acid sequence:

(SEQ ID NO: 17)
aggaacccctagtgatggagttggccactccctctctgcgcgctcgctc
gctcactgaggccgggcgaccaaaggtcgcccgacgcccgggctttgcc
cgggggcctcagtgagcgagcgagcgcgcagctgcctgcagg.

In some embodiments, the expression cassette includes a nucleic acid with the nucleotide sequence (SEQ ID NO: 6)
cctgcaggcagctgcgcgctcgctcgctcactgaggccgcccgggcgtcgggcgacctttggtcgcccggcctcagtgagcgagc gagcgcgcagagagggagtggccaactccatcactaggggttcctgcggccgcacgcgtctagttattaatagtaatcaattacggg gtcattagttcatagcccatatatggagttccgcgttacataacttacggtaaatggcccgcctggctgaccgcccaacgacccccgcc cattgacgtcaataatgacgtatgttcccatagtaacgCcaatagggactttccattgacgtcaatgggtggagtatttacggtaaactgc ccacttggcagtacatcaagtgtatcatatgccaagtacgccccctattgacgtcaatgacggtaaatggcccgcctggcattatgccca gtacatgaccttatgggactttcctacttggcagtacatctacgtattagtcatcgctattaccatggtgatgcggttttggcagtacatcaat gggcgtggatagcggtttgactcacggggatttccaagtctccaccccattgacgtcaatgggagtttgttttgGcaccaaaatcaacg ggactttccaaaatgtcgtaacaactccgccccattgacgcaaatgggcggtaggcgtgtacggtgggaggtctatataagcagagct cgtttagtgaaccgtcagatcgcctggagacgccatccacgctgttttgacctccatagaagacaccgggaccgatccagcctccgcg gattcgaatcccggccgggaacggtgcattggaacgcggattccccgtgccaagagtgacgtaagtaccgcctatagagtctatagg cccacaaaaaatgctttcttcttttaatatactttttttgtttatcttatttctaatactttccctaatctctttctttcagggcaataatgata caatgtatcatgcctctttgcaccattctaaagaataacagtgataatttctgggttaaggcaatagcaatatttctgcatataaatatttctg catataaattgtaactgatgtaagaggtttcatattgctaatagcagctacaatccagctaccattctgcttttattttatggttgggataagg ctggattattctgagtccaagctaggcccttttgctaatcatgttcatacctcttatcttcctcccacagctcctgggcaacgtgctggtctgt gtgctggcccatcactttggcaaagaattgggattcgaacatCGATTGTAATTCATGAGCCACCATGGCCATGAGCA

GCGGCGGCAGCGGCGGCGGCGTGCCTGAGCAAGAGGACAGCGTGCTGTTCAGAA

GAGGCACCGGCCAGAGCGACGACAGCGACATCTGGGACGACACCGCCCTGATCA

AGGCCTACGACAAGGCCGTGGCCAGCTTCAAGCACGCCCTGAAGAACGGCGACA

TCTGCGAGACCAGCGGCAAGCCCAAGACCACCCCCAAGAGAAAGCCCGCCAAG

AAGAACAAGAGCCAGAAGAAGAACACCGCCGCCAGCCTGCAGCAGTGGAAGGT

GGGCGACAAGTGCAGCGCCATCTGGAGCGAGGACGGCTGCATCTACCCCGCCAC

CATCGCCAGCATCGACTTCAAGAGAGAGACCTGCGTGGTGGTGTACACCGGCTA

CGGCAACAGAGAGGAGCAGAACCTGAGCGACCTGCTGAGCCCCATCTGCGAGGT

GGCCAACAACATCGAGCAGAACGCCCAAGAGAACGAGAACGAGAGCCAAGTGA

GCACCGACGAGAGCGAGAACAGCAGAAGCCCCGGCAACAAGAGCGACAACATC

AAGCCCAAGAGCGCCCCCTGGAACAGCTTCCTGCCCCCTCCCCCCCCTATGCCCG

GCCCTAGACTGGGCCCTGGCAAGCCTGGCCTGAAGTTCAACGGCCCCCCCCCCC

TCCTCCTCCTCCTCCTCCTCACCTGCTGAGCTGCTGGCTGCCCCCCTTCCCCAGCG

GCCCTCCTATCATCCCTCCTCCCCCCCCCATCTGCCCCGACAGCCTGGACGACGC

CGACGCCCTGGGCAGCATGCTGATCAGCTGGTACATGAGCGGCTACCACACCGG

CTACTACATGGGCTTCAGACAGAACCAGAAGGAGGGCCGGTGCAGCCACAGCCT

GAACTGATctagagtcgacctgcagaagcttgcctcgagcagcgctgctcgagagatctacgggtggcatccctgtgacccct ccccagtgcctctcctggccctggaagttgccactccagtgcccaccagccttgtcctaataaaattaagttgcatcattttgtctgactag gtgtccttctataatattatggggtggaggggggtggtatggagcaaggggcaagttgggaagacaacctgtagggcctgcggggtc -continued

```
tattgggaaccaagctggagtgcagtggcacaatcttggctcactgcaatctccgcctcctgggttcaagcgattctcctgcctcagcct

cccgagttgttgggattccaggcatgcatgaccaggctcagctaatttttgtttttttggtagagacggggtttcaccatattggccaggct

ggtctccaactcctaatctcaggtgatctacccaccttggcctcccaaattgctgggattacaggcgtgaaccactgctcccttccctgtc

cttctgattttgtaggtaaccacTAGAGAAATGTTCTGGCACCTGCACttgcactggggacagcctattttgctag

tttgttttgtttcgttttgttttgatggagagcgtatgttagtactatcgattcacacaaaaaccaacacacagatgtaatgaaaataaagat

attttattgcggccgcTGTTCCTGCTGAACTGAGCCAGTGTACACAAACCAACTGTGTTTCA

GCTCAGTAGGCACGGGAGGCAGAGCCCAGGGAGGCCAGGCAGCAGGATGGCAG

GCAGACAGGCGGCAGCAGGGGACAGGCGGCAAGGCCAGAGGAGGTGAGGGCCT

GGGGGGCGGAACTTAGCCACTGTGAACACGACTTGGTGTGGACCCTGCTCACAA

GCAGCTAAGCCCTGCTCCTCAGGCCAGGCACAGGCTTCGGGGCCTCTCTGCCACC

CCGTCCCCGGGCAGCATCCTCGGTGGCAGAGCTCAGGGTCGGTTGGAAATCCCT

GGCAATGTGATTTGTGACAGGAAGCAAATCCCATCCCCAGGAACCCCAGCCGGC

CGTGGCACAGGGGTGAGGGGGGCACCGGGCGGGGCCAGAGGCTGGCACCTGGA

GGGGAGAAAGAGAGAGAGAGCAAAGGAGGTAATGAGATTTGGGGACACCTCCC

CTCCAGGTCCCCAGATGCTTCCTTTGATCACAGGGAAGCTCTTTTCTCATATGCA

GGAGCCACCACACGGGGAGCTGGAGCCTAGCTGTGCCCTCCGTTCCAGCCCCAG

GACTGGAGAGGCAGAGATACCTAGAGGGCCCATGCGGGACAAGGAGGCTACAG

CAACTTGCATGgccgcagcttttttgcaaaagcctaggcctccaaaaaagcctcctcactacttctggaatagctcagaggcc

gaggcggcctcggcctctgcataaataaaaaaaattagtcagcgatggggcggagaatgggcggaactgggcggagttaggggcg

ggatgggcggagttaggggcgggaCTATGGTTGCTGACTAATTGAGATGCAgggccgctccaagtacctc

ccgtaccttaagtgcggaccgagcggccgcaggaacccctagtgatggagttggccactccctctctgcgcgctcgctcgctcactg

aggccgggcgaccaaaggtcgcccgacgcccgggctttgcccgggcggcctcagtgagcgagcgagcgcgcagctgcctgcag

g.
```

In one aspect, the present invention relates to an expression vector that includes any of the above nucleic acids or any of the above cassettes.

In some embodiments, a vector is a plasmid, i.e., a circular double stranded piece of DNA into which additional DNA segments may be ligated.

In some embodiments, a vector is a viral vector, wherein additional DNA segments may be ligated into the viral genome.

In some embodiments, vectors are capable of autonomous replication in a host cell into which they are introduced (e.g. bacterial vectors having a bacterial origin site of replication and episomal mammalian vectors). In further embodiments, vectors (e.g. non-episomal mammalian vectors) may be integrated into the genome of a host cell upon introduction into a host cell, and thereby are replicated along with the host gene. Moreover, certain vectors are capable of directing the expression of genes to which they are operably linked. Such vectors are referred to herein as "recombinant expression vectors" (or simply, "expression vectors").

Expression vectors include plasmids, retroviruses, adenoviruses, adeno-associated viruses (AAVs), plant viruses, such as cauliflower mosaic virus, tobacco mosaic virus, cosmids, YACs, EBV derived episomes, and the like. DNA molecules may be ligated into a vector such that transcriptional and translational control sequences within the vector serve their intended function of regulating the transcription and translation of the DNA. An expression vector and expression control sequences may be chosen to be compatible with the expression host cell used. DNA molecules may be introduced into the expression vector by standard methods (e.g. ligation of complementary restriction sites, or blunt end ligation if no restriction sites are present).

The recombinant expression vector may also encode a leader peptide (or a signal peptide) that facilitates the secretion of the protein of interest from a host cell. The gene of the protein of interest may be cloned into the vector such that the signal peptide is linked in-frame to the amino terminus of the protein of interest. The leader peptide (or signal peptide) may be an immunoglobulin leader peptide or other leader peptide (that is, a non-immunoglobulin protein leader peptide).

In addition to the SMN1 and microRNA miR-23a genes according to the present invention, the recombinant expression of the vectors according to the present invention may carry regulatory sequences that control the expression of the SMN1 gene and microRNA miR-23a gene in a host cell. It will be understood by those skilled in the art that the design of an expression vector, including the selection of regulatory sequences, may depend on such factors as the choice of a host cell to be transformed, the level of expression of a desired protein, and so forth. Preferred control sequences for an expression host cell in mammals include viral elements that ensure high levels of protein expression in mammalian cells, such as promoters and/or enhancers derived from a retroviral LTR, cytomegalovirus (CMV) (such as a CMV promoter/enhancer), simian virus 40 (SV40) (such as a SV40 promoter/enhancer), adenovirus, (e.g. the major late promoter adenovirus (AdMLP)), polyomavirus and strong mammalian promoters such as native immunoglobulin promoter or actin promoter.

The term "control sequences" refers to DNA sequences necessary for the expression of an operably linked coding sequence in a particular host organism. The control sequences that are suitable for prokaryotes are, for example, a promoter, optionally an operator sequence and a ribosome binding site. Eukaryotic cells are known to include promoters, polyadenylation signals, and enhancers.

As used in the present description, the term "promoter" or "transcription regulatory sequence" or "regulatory sequence" refers to a nucleic acid fragment that controls the transcription of one or more coding sequences, and that is located upstream with respect to the direction of reading relative to the direction of transcription from the transcription initiation site of the coding sequence, and is structurally identified by the presence of a binding site for DNA-dependent RNA polymerase, transcription initiation sites and any other DNA sequences, including, but not limited to, transcription factor binding sites, repressor and activator protein binding sites, and any other sequences of nucleotides known to one of skill in the art that directly or indirectly regulate the level of transcription with said promoter. A "constitutive" promoter is a promoter that is active in most tissues under typical physiological and developmental conditions. An "inducible" promoter is a promoter that is physiologically or developmentally regulated, e.g. under the influence of a chemical inducer. A "tissue specific" promoter is only active in specific types of tissues or cells.

The terms "enhancers" or "enhancer" as used herein may refer to a DNA sequence that is located adjacent to the DNA sequence that encodes a recombinant product. Enhancer elements are typically located in a 5' direction from a promoter element or can be located downstream of or within a coding DNA sequence (e.g. a DNA sequence transcribed or translated into a recombinant product or products). Hence, an enhancer element may be located 100 base pairs, 200 base pairs, or 300 or more base pairs upstream of a DNA sequence that encodes a recombinant product, or downstream of said sequence. Enhancer elements may increase the amount of a recombinant product being expressed from a DNA sequence above the level of expression associated with a single promoter element. Multiple enhancer elements are readily available to those of ordinary skill in the art.

The term "expression control sequence" as used in the present description refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include the promoter of ribosome binding site, and transcription termination sequences; in eukaryotes, typically, such control sequences include promoters and transcription termination sequences. The term "control sequences" includes at least all components, the presence of which is essential for expression and processing, and can also include additional components, the presence of which is advantageous, for example, leader sequences and fusion partner sequences.

In one embodiment of the present invention, "expression vector" relates to a vector comprising one or more polynucleotide sequences of interest, genes of interest, or "transgenes" that are flanked by parvoviral sequences or inverted terminal repeat (ITR) sequences.

Neither the cassette nor the vector of the invention comprises nucleotide sequences of genes encoding non-structural proteins (Rep) and structural proteins (Cap) of the adeno-associated virus.

AAV9 (Adeno-Associated Virus Serotype 9)-Based Recombinant Virus

In one aspect, the present invention relates to an AAV9 (adeno-associated virus serotype 9)-based recombinant virus for the expression of the SMN1 gene in target cells, which includes a capsid and any of the above expression cassettes.

The term "AAV-based recombinant virus" (or "AAV-based virus-like particle", or "AAV recombinant virus strain", or "AAV recombinant vector", or "rAAV vector") as used in this description refers to the above expression cassette (or the above expression vector), which is enclosed within the AAV capsid.

The Cap gene, among other alternative products, encodes 3 capsid proteins (VP1, VP2, and VP3). VP1, VP2, and VP3 are present at 1:1:10 ratio to form an icosahedral capsid (Xie Q. et al. The atomic structure of adeno-associated virus (AAV-2), a vector for human gene therapy. Proc Natl Acad Sci USA, 2002; 99:10405-10410). Transcription of these genes starts from a single promoter, p40. The molecular weights of the corresponding proteins (VP1, VP2 и VP3) are 87, 72, and 62 kDa, respectively. All of the three proteins are translated from a single mRNA. Following transcription, pre-mRNA may be spliced in two different manners, where either longer or shorter intron is excised to form mRNAs of various nucleotide lengths.

During the production of the AAV (rAAV)-based recombinant virus, an expression cassette flanked by ITR is packaged into an AAV capsid. The genes required for AAV replication, as mentioned above, are not included in the cassette.

The expression cassette DNA is packaged into a viral capsid in the form of a single stranded DNA molecule (ssDNA) being approximately 3000 nucleotides long. Once a cell is infected with the virus, the single-stranded DNA is converted to the form of double-stranded DNA (dsDNA). The dsDNA can only be used by the cell's proteins, which transcribe the present gene or genes into RNA.

In some embodiments, the AAV9-based recombinant virus has a capsid that includes the AAV9 protein VP1.

In some embodiments, the AAV9-based recombinant virus has a capsid that includes the AAV9 protein VP1 having the following amino acid sequence

```
                                       (SEQ ID NO: 7)
MAADGYLPDWLEDNLSEGIREWWALKPGAPQPKANQQHQDNARGLVLPG

YKYLGPGNGLDKGEPVNAADAAALEHDKAYDQQLKAGDNPYLKYNHADA

EFQERLKEDTSFGGNLGRAVFQAKKRLLEPLGLVEEAAKTAPGKKRPVE

QSPQEPDSSAGIGKSGAQPAKKRLNFGQTGDTESVPDPQPIGEPPAAPS

GVGSLTMASGGGAPVADNNEGADGVGSSSGNWHCDSQWLGDRVITTSTR
```

-continued

TWALPTYNNHLYKQISNSTSGGSSNDNAYFGYSTPWGYFDFNRFHCHFS

PRDWQRLINNNWGFRPKRLNFKLFNIQVKEVTDNNGVKTIANNLTSTVQ

VFTDSDYQLPYVLGSAHEGCLPPFPADVFMIPQYGYLTLNDGSQAVGRS

SFYCLEYFPSQMLRTGNNFQFSYEFENVPFHSSYAHSQSLDRLMNPLID

QYLYYLSKTINGSGQNQQTLKFSVAGPSNMAVQGRNYIPGPSYRQQRVS

TTVTQNNNSEFAWPGASSWALNGRNSLMNPGPAMASHKEGEDRFFPLSG

SLIFGKQGTGRDNVDADKVMITNEEEIKTTNPVATESYGQVATNHQSAQ

AQAQTGWVQNQGILPGMVWQDRDVYLQGPIWAKIPHTDGNFHPSPLMGG

FGMKHPPPQILIKNTPVPADPPTAFNKDKLNSFITQYSTGQVSVEIEWE

LQKENSKRWNPEIQYTSNYYKSNNVEFAVNTEGVYSEPRPIGTRYLTRN

L.

In some embodiments, the AAV9-based recombinant virus has a capsid that includes the AAV9 protein VP1 having the amino acid sequence of SEQ ID NO: 7 with one or more point mutations.

In some embodiments, the AAV9-based recombinant virus has a capsid that includes the AAV9 protein VP2.

In some embodiments, the AAV9-based recombinant virus has a capsid that includes the AAV9 protein VP2 having the following amino acid sequence:

(SEQ ID NO: 8)

TAPGKKRPVEQSPQEPDSSAGIGKSGAQPAKKRLNFGQTGDTESVPDPQ

PIGEPPAAPSGVGSLTMASGGGAPVADNNEGADGVGSSSGNWHCDSQWL

GDRVITTSTRTWALPTYNNHLYKQISNSTSGGSSNDNAYFGYSTPWGYF

DFNRFHCHFSPRDWQRLINNNWGFRPKRLNFKLFNIQVKEVTDNNGVKT

IANNLTSTVQVFTDSDYQLPYVLGSAHEGCLPPFPADVFMIPQYGYLTL

NDGSQAVGRSSFYCLEYFPSQMLRTGNNFQFSYEFENVPFHSSYAHSQS

LDRLMNPLIDQYLYYLSKTINGSGQNQQTLKFSVAGPSNMAVQGRNYIP

GPSYRQQRVSTTVTQNNNSEFAWPGASSWALNGRNSLMNPGPAMASHKE

GEDRFFPLSGSLIFGKQGTGRDNVDADKVMITNEEEIKTTNPVATESYG

QVATNHQSAQAQAQTGWVQNQGILPGMVWQDRDVYLQGPIWAKIPHTDG

NFHPSPLMGGFGMKHPPPQILIKNTPVPADPPTAFNKDKLNSFITQYST

GQVSVEIEWELQKENSKRWNPEIQYTSNYYKSNNVEFAVNTEGVYSEPR

PIGTRYLTRNL.

In some embodiments, the AAV9-based recombinant virus has a capsid that includes the AAV9 protein VP2 having the amino acid sequence of SEQ ID NO: 8 with one or more point mutations.

In some embodiments, the AAV9-based recombinant virus has a capsid that includes the AAV9 protein VP3.

In some embodiments, the AAV9-based recombinant virus has a capsid that includes the AAV9 protein VP3 having the following amino acid sequence (SEQ ID NO: 9)

MASGGGAPVADNNEGADGVGSSSGNWHCDSQWLGDRVITTSTRTWALPT

YNNHLYKQISNSTSGGSSNDNAYFGYSTPWGYFDFNRFHCHFSPRDWQR

-continued

LINNNWGFRPKRLNFKLFNIQVKEVTDNNGVKTIANNLTSTVQVFTDSD

YQLPYVLGSAHEGCLPPFPADVFMIPQYGYLTLNDGSQAVGRSSFYCLE

YFPSQMLRTGNNFQFSYEFENVPFHSSYAHSQSLDRLMNPLIDQYLYYL

SKTINGSGQNQQTLKFSVAGPSNMAVQGRNYIPGPSYRQQRVSTTVTQN

NNSEFAWPGASSWALNGRNSLMNPGPAMASHKEGEDRFFPLSGSLIFGK

QGTGRDNVDADKVMITNEEEIKTTNPVATESYGQVATNHQSAQAQAQTG

WVQNQGILPGMVWQDRDVYLQGPIWAKIPHTDGNFHPSPLMGGFGMKHP

PPQILIKNTPVPADPPTAFNKDKLNSFITQYSTGQVSVEIEWELQKENS

KRWNPEIQYTSNYYKSNNVEFAVNTEGVYSEPRPIGTRYLTRNL.

In some embodiments, the AAV9-based recombinant virus has a capsid that includes the AAV9 protein VP3 having the amino acid sequence of SEQ ID NO: 9 with one or more point mutations.

In some embodiments, the AAV9-based recombinant virus has a capsid that includes the AAV9 proteins VP1, VP2, and VP3.

In some embodiments, the AAV9-based recombinant virus has a capsid that includes the proteins VP1 having the amino acid sequence of SEQ ID NO: 7, VP2 having the amino acid sequence of SEQ ID NO: 8, and VP3 having the amino acid sequence of SEQ ID NO: 9.

In some embodiments, the AAV9-based recombinant virus has a capsid that includes the proteins VP1 having the amino acid sequence of SEQ ID NO: 7 with one or more point mutations, VP2 having the amino acid sequence of SEQ ID NO: 8 with one or more point mutations, and VP3 having the amino acid sequence of SEQ ID NO: 9 with one or more point mutations.

The phrase "more point mutations" refers to two, three, four, five, six, seven, eight, nine, or ten point substitutions.

Particularly preferred embodiments include substitutions (mutations) that are conservative in nature, i.e. substitutions that take place within a family of amino acids that are joined in their side chains. In particular, amino acids are typically divided into four families: (1) acidic amino acids are aspartate and glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. Phenylalanine, tryptophan, and tyrosine are sometimes classified as aromatic amino acids. For example, it is reasonably predictable that an isolated substitution of leucine for isoleucine or valine, an aspartate for a glutamate, a threonine for a serine, or a similar conservative substitution of an amino acid for a structurally related amino acid, will not have a major effect on the biological activity. For example, the polypeptide of interest may include up to about 5-10 conservative or non-conservative amino acid substitutions, so long as the desired function of the molecule remains intact.

An embodiment with point mutations in the sequences of AAV9 proteins VP1, VP2, or VP3 using amino acid substitutions is a substitution of at least one amino acid residue in the AAV9 protein VP1, VP2, or VP3 with another amino acid residue.

Conservative substitutions are shown in Table A under "preferred substitutions".

TABLE A

| Original residue | Exemplary substitutions | Preferred substitutions |
|---|---|---|
| Ala (A) | Val; Leu; Ile | Val |
| Arg(R) | Lys; Gin; Asn | Lys |
| Asn(N) | Gin; His; Asp, Lys; Arg | Gin |
| Asp (D) | Glu; Asn | Glu |
| Cys (C) | Ser; Ala | Ser |
| Gln(Q) | Asn; Glu | Asn |
| Glu (E) | Asp; Gin | Asp |
| Gly(G) | Ala | Ala |
| His (H) | Asn; Gin; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gin; Asn | Arg |
| Met (M) | Leu; Phe; Ile | Leu |
| Phe(F) | Trp; Leu; Val; Ile; Ala; Tyr | Tyr |
| Pro (P) | Ala | Ala |
| Ser(S) | Thr | Thr |
| Thr (T) | Val; Ser | Ser |
| Trp(W) | Tyr; Phe | Tyr |
| Tyr(Y) | Trp; Phe; Thr; Ser | Phe |
| Val (V) | Ile; Leu; Met; Phe; Ala; Norleucine | Leu |

In some embodiments, the AAV9-based recombinant virus has a capsid that includes the AAV9 protein VP1 having the amino acid sequence of SEQ ID NO: 7 or the amino acid sequence of SEQ ID NO: 7 with one or more point mutations, and the expression cassette includes the following elements in the 5'-end to 3'-end direction:

a left-hand (first) ITR (inverted terminal repeats);
a CMV (cytomegalovirus) enhancer;
a CMV (cytomegalovirus) promoter;
an intron of the hBG1 gene (hemoglobin subunit gamma 1 gene);
a nucleic acid that encodes the SMN1 protein;
an hGH1 polyadenylation signal (human growth hormone gene polyadenylation signal);
an SV40 promoter (simian virus 40 promoter);
a nucleic acid that encodes the microRNA miR-23a;
an SV40 polyadenylation signal (simian virus 40 polyadenylation signal), and
a right-hand (second) ITR.

In some embodiments, the AAV9-based recombinant virus has a capsid that includes the proteins VP1 having the amino acid sequence of SEQ ID NO: 7, VP2 having the amino acid sequence of SEQ ID NO: 8, and VP3 having the amino acid sequence of SEQ ID NO: 9, and the expression cassette includes the following elements in the 5'-end to 3'-end direction:

a left-hand (first) ITR (inverted terminal repeats);
a CMV (cytomegalovirus) enhancer;
a CMV (cytomegalovirus) promoter;
an intron of the hBG1 gene (hemoglobin subunit gamma 1 gene);
a nucleic acid that encodes the SMN1 protein;
an hGH1 polyadenylation signal (human growth hormone gene polyadenylation signal);
an SV40 promoter (simian virus 40 promoter);
a nucleic acid that encodes the microRNA miR-23a;
an SV40 polyadenylation signal (simian virus 40 polyadenylation signal), and
a right-hand (second) ITR.

In some embodiments, the AAV9-based recombinant virus has a capsid that includes the proteins VP1 having the amino acid sequence of SEQ ID NO: 7 with one or more point mutations, VP2 having the amino acid sequence of SEQ ID NO: 8 with one or more point mutations, and VP3 having the amino acid sequence of SEQ ID NO: 9 with one or more point mutations, and the expression cassette includes the following elements in the 5'-end to 3'-end direction:

a left-hand (first) ITR (inverted terminal repeats);
a CMV (cytomegalovirus) enhancer;
a CMV (cytomegalovirus) promoter;
an intron of the hBG1 gene (hemoglobin subunit gamma 1 gene);
a nucleic acid that encodes the SMN1 protein;
an hGH1 polyadenylation signal (human growth hormone gene polyadenylation signal);
an SV40 promoter (simian virus 40 promoter);
a nucleic acid that encodes the microRNA miR-23a;
an SV40 polyadenylation signal (simian virus 40 polyadenylation signal), and
a right-hand (second) ITR.

In some embodiments, the AAV9-based recombinant virus has a capsid that includes the AAV9 protein VP1 having the amino acid sequence of SEQ ID NO: 7 or the amino acid sequence of SEQ ID NO: 7 with one or more point mutations, and the expression cassette comprises a nucleic acid with SEQ ID NO: 6.

In some embodiments, the AAV9-based recombinant virus has a capsid that includes the proteins VP1 having the amino acid sequence of SEQ ID NO: 7, VP2 having the amino acid sequence of SEQ ID NO: 8, and VP3 having the amino acid sequence of SEQ ID NO: 9, and the expression cassette comprises a nucleic acid with SEQ ID NO: 6.

In some embodiments, the AAV9-based recombinant virus has a capsid that includes the proteins VP1 having the amino acid sequence of SEQ ID NO: 7 with one or more point mutations, VP2 having the amino acid sequence of SEQ ID NO: 8 with one or more point mutations, and VP3 having the amino acid sequence of SEQ ID NO: 9 with one or more point mutations, and the expression cassette comprises a nucleic acid with SEQ ID NO: 6.

Pharmaceutical Composition

In one aspect, the present invention relates to a pharmaceutical composition for delivering the SMN1 gene to target cells, which includes any of the above AAV9-based recombinant viruses in combination with one or more pharmaceutically acceptable excipients.

The active substance in the above composition is present in an effective amount, for example, in a biologically effective amount.

In particular embodiments, the present invention relates to a pharmaceutical composition comprising the AAV9-based recombinant virus of the invention in a pharmaceutically acceptable carrier or in other pharmaceutical agents, adjuvants, diluents, etc. For injection, the carrier will typically be a liquid carrier. For other methods of administration, the carrier may be either solid or liquid, such as sterile pyrogen-free water or sterile pyrogen-free phosphate-buffered saline solution. For inhalation administration, the carrier is respirable, and preferably is in a solid or liquid particulate form. As an injection medium, it is preferred to use water that contains the additives that are common for injection solutions, such as stabilizing agents, salts or saline, and/or buffers.

"Pharmaceutical composition" means a composition comprising the above AAV9-based recombinant virus of the invention and at least one of components selected from the group consisting of pharmaceutically acceptable and pharmacologically compatible excipients, such as fillers, solvents, diluents, carriers, auxiliary, distributing agents, delivery agents, preservatives, stabilizers, emulsifiers, suspending agents, thickeners, prolonged delivery controllers, the choice and proportions of which depend on the type and route of administration and dosage. Pharmaceutical compositions of the present invention and methods of preparation thereof will be undoubtedly apparent to those skilled in the art. The pharmaceutical compositions should preferably be manufactured in compliance with the GMP (Good Manufacturing Practice) requirements. The composition may comprise a buffer composition, tonicity agents, stabilizers and solubilizers.

"Pharmaceutically acceptable" means a material that does not have biological or other negative side effects, for example, the material can be administered to a subject without causing any undesirable biological effects. Thus, such pharmaceutical compositions may be used, for example, in transfection of a cell ex vivo or in administration in vivo of the AAV9-based recombinant virus of the invention directly to a subject.

The term "excipient" is used herein to describe any ingredient other than the above ingredients of the invention. These are substances of inorganic or organic nature which are used in the pharmaceutical manufacturing in order to give drug products the necessary physicochemical properties.

"Stabilizer" refers to an excipient or a mixture of two or more excipients that provide the physical and/or chemical stability of the active agent.

The term "buffer", "buffer composition", "buffering agent" refers to a solution, which is capable of resisting changes in pH by the action of its acid-base conjugate components, which allows the rAAV9 vector product to resist changes in pH. Generally, the pharmaceutical composition preferably has a pH in the range from 4.0 to 8.0. Examples of buffers used include, but are not limited to, acetate, phosphate, citrate, histidine, succinate, etc. buffer solutions.

The pharmaceutical composition is "stable" if the active agent retains physical stability and/or chemical stability and/or biological activity thereof during the specified shelf life at storage temperature, for example, of 2-8° C. Preferably, the active agent retains both physical and chemical stability, as well as biological activity. Storage period is adjusted based on the results of stability test in accelerated or natural aging conditions.

A pharmaceutical composition of the invention can be manufactured, packaged, or widely sold in the form of a single unit dose or a plurality of single unit doses in the form of a ready formulation. The term "single unit dose" as used herein refers to discrete quantity of a pharmaceutical composition containing a predetermined quantity of an active ingredient. The quantity of the active ingredient typically equals the dose of the active ingredient to be administered in a subject, or a convenient portion of such dose, for example, half or a third of such dose.

Use

The authors of the invention surprisingly found that miR-23a enhances the functional effect of SMN1 in vitro and revealed the synergistic effect of SMN1 and miR-23a in treating SMA in an animal model of the disease.

In one aspect, the present invention relates to the use of any of the above AAV9-based recombinant viruses or the above composition to deliver the SMN1 gene to target cells.

In one aspect, the present invention relates to the use of any of the above AAV9-based recombinant viruses or the above composition for survival of a subject that has spinal muscular atrophy and/or that does not have fully functional copies of the SMN1 gene.

In one aspect, the present invention relates to the use of any of the above AAV9-based recombinant viruses or the above composition for providing the SMN1 protein to a subject that has spinal muscular atrophy and/or that does not have fully functional copies of the SMN1 gene.

In one aspect, the present invention relates to the use of any of the above AAV9-based recombinant viruses or the above composition for treating spinal muscular atrophy in a subject that has spinal muscular atrophy.

In one aspect, the present invention relates to a method for modulating motor function in a subject having a motor neuron disorder, said method comprising administering a therapeutically effective amount of any of the above AAV9-based recombinant viruses or the above composition into the cells of the subject.

In one aspect, the present invention relates to a method for providing the SMN protein to a subject having spinal muscular atrophy, said method comprising administering a therapeutically effective amount of any of the above AAV9-based recombinant viruses or the above composition into the cells of the subject in need thereof.

In one aspect, the present invention relates to a method for delivering the SMN1 gene to the target cells of a subject having spinal muscular atrophy, said method comprising administering any of the above AAV9-based recombinant viruses or the above composition into the cells of the subject.

In one aspect, the present invention relates to a method for treating spinal muscular atrophy in a subject, said method comprising administering a therapeutically effective amount of any of the above AAV9-based recombinant viruses or the above composition into a subject having spinal muscular atrophy.

The lack of fully functional copies of the SMN1 gene refers to inactivating mutations or deletions in all copies of the SMN1 gene in the genome, which result in the loss or defect of the function of the SMN1 gene.

Subject refers to any animal that is amenable to the techniques provided in the present description. In certain non-limiting embodiments, the subject is a human. Said subject may be either male or female, of any age.

A subject in need of delivering the SMN1 gene to target cells, or a subject in need of being provided with the SMN1 protein, or a subject in need of delivering the SMN1 gene to target cells refers to a subject who has spinal muscular atrophy or a subject who has inactivating mutations or deletions in the SMN1 gene that lead to loss or defect in the function of the SMN1 gene.

Exemplary modes of administration include topical application, intranasal, inhalation, transmucosal, transdermal, enteral (e.g. oral, rectal), parenteral (e.g. intravenous, subcutaneous, intradermal, intramuscular) administrations, as well as direct tissue or organ injections.

Injectables can be prepared in conventional forms, either as liquid solutions or suspensions, solid forms suitable for the preparation of solution or suspensions in liquid prior to injection, or as emulsions. Alternatively, one may administer the above AAV9-based recombinant virus of the present invention in a local rather than systemic manner, for example in a depot or sustained-release formulation.

The AAV9-based recombinant virus is introduced into an organism in an effective amount. The AAV9-based recombinant virus is preferably introduced into an organism in a biologically effective amount. A "biologically effective" amount of the recombinant virus is an amount that is sufficient to cause infection (or transduction) and expression of the nucleic acid sequence in the cell. If the virus is administered to a cell in vivo (e.g. the virus is administered to a subject, as described below), a "biologically-effective" amount of the viral vector is an amount that is sufficient to cause the transduction and expression of the nucleic acid sequence in the target cell.

Dosages of the above AAV9-based recombinant virus of the invention will depend on the mode of administration, the particular viral vector, and they can be determined in a routine manner. Exemplary doses for achieving therapeutic effects are viral titers of at least about $10^5$, $10^6$, $10^7$, $10^8$, $10^9$, $10^{10}$, $10^{11}$, $10^{12}$, $10^{13}$, $10^{14}$, $10^{15}$, $10^{16}$ transducing units or more, preferably about $10^9$ to $10^{15}$ transducing units, yet more preferably $10^{14}$ transducing units per kilogram.

The cell for administering the above AAV9-based recombinant virus of the invention may be a cell of any type, including but not limited to motor neurons or other tissues of the nervous system, epithelial cells (e.g. skin, respiratory and gut epithelial cells), hepatic cells, muscle cells, pancreatic cells (including islet cells), hepatic cells, spleen cells, fibroblasts, endothelial cells, and the like.

The above AAV9-based recombinant virus of the invention is not used to modify the genetic integrity of human germ line cells.

EXAMPLES

The following examples are provided for better understanding of the invention. These examples are for purposes of illustration only and are not to be construed as limiting the scope of the invention in any manner.

All publications, patents, and patent applications cited in this specification are incorporated herein by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended embodiments.

Materials and General Methods

Recombinant DNA Techniques

Standard methods were used to manipulate DNA as described in Sambrook, J. et al, Molecular cloning: A laboratory manual; Cold Spring Harbor Laboratory Press, Cold Spring Harbor, New York, 1989. The molecular biological reagents were used according to the manufacturer protocols. Briefly, plasmid DNA was produced for further manipulation in *E. coli* cells grown under selective antibiotic pressure so that the plasmids were not lost in the cell population. We isolated the plasmid DNA from cells using commercial kits, measured the concentration, and used it for cloning by restriction endonuclease treatment or PCR amplification. The DNA fragments were ligated to each other using ligases and transformed into bacterial cells for the selection of clones and further production. All resulting genetic constructs were confirmed by restriction patterns and complete Sanger sequencing.

Gene Synthesis

Desired gene segments were prepared from oligonucleotides made by chemical synthesis. Gene segments of 300 to 1000 bp long, which were flanked by unique restriction sites, were collected by renaturing oligonucleotides on top of each other, followed by PCR amplification from border primers. As a result, a mixture of fragments was produced, including the desired one. The fragments were cloned at restriction sites into intermediate vectors, following which the DNA sequences of the subcloned fragments were confirmed by DNA sequencing.

DNA Sequence Determination

DNA sequences were determined by Sanger sequencing. DNA and protein sequences were analyzed and sequence data was processed in SnapGene Viewer 4.2 or higher for sequence creation, mapping, analysis, annotation and illustration.

Culturing Cell Cultures

The experiments used HEK293 (Human Embryonic Kidney clone 293) and U-87 MG (human glioblastoma) cell lines. The cells were cultured under standard conditions at 37° C. and 5% $CO_2$, on a DMEM complete culture medium supplemented with 10% FBS and an antibiotic. To culture HSMCs, the culture plastic was pre-coated with collagen (Gibco). Cells were subcultured upon reaching 80-90% confluence. Cell viability was assessed using either Trypan Blue stain and a hemocytometer or PI stain and flow cytometry.

siRNA Cell Transfection

A commercial siRNA specific for the SMN1 gene was ordered from the manufacturer (ThermoFisher Scientific) along with a non-specific control.

Cell lines were inoculated the day before transfection into 6-well plates such that they reached 70-80% confluence by the time of transfection. Transfection was performed using commercial lipofection kits according to the manufacturer's protocol. 24 h following transfection, transduction was performed (see below). 120 h following transduction, the cells were treated with trypsin solutions or similar, removed from the substrate, washed in a phosphate buffer, and collected for further analysis of expression of target genes and proteins. Enzyme immunoassay (ELISA) was performed to control the level of SMN protein knockdown.

All samples were analyzed with 3 experimental replicates.

Gene Expression Analysis

Expression of SMN1 at the mRNA level and expression of miR-23a was measured using quantitative PCR. Briefly, we used primers and a sample that are specific for the nucleotide sequence encoding the SMN1 protein. For miR-23a, we used a commercial kit for quantitative PCR specific for processed miR-23a (Thermo Fisher Scientific). Primers and a sample specific for the GAPDH household gene were used to control the initial RNA levels. Calibration curves were plotted for each set of primers and samples using a known copy number of linearized plasmid DNA comprising the amplified sequence of the corresponding gene. Expression was analyzed by determining, using the calibration curves, the copy number of SMN1 and GAPDH in each sample, following which we normalized the copy number of SMN1 to 10,000 copies of GAPDH. The resulting values were compared for different samples within the same experiment.

Determination of SMN Protein Expression

Thermo Fisher Scientific kit was used to determine the amount of total protein. Cellular precipitates were lysed, the resulting lysates were introduced into microplate wells together with standard dilutions of BSA at a known concentration. A working reagent was added to the samples, and the samples were incubated. At the end of incubation, we measured absorption at a wavelength of 562 nm on a microplate reader. Concentration of total protein in test samples was calculated according to BSA standard curve. Next, the lysates were diluted to a total protein concentration of 10 μg/ml.

Content of SMN protein in cells was assessed by enzyme immunoassay (ELISA) using a commercial Abcam kit according to the manufacturer's instructions. Microplate wells coated with anti-SMN antibodies were loaded with test samples and standards at known concentrations. Following incubation and washing, SMN-specific polyclonal antibodies for detection were added to each well, the samples were incubated and washed. Secondary antibodies conjugated with horseradish peroxidase were added, and the samples were incubated. Excess of reagents was washed off and TMB substrate was added. Following a short-term incubation, the enzymatic reaction was stopped with stop reagent. Optical density of the yellow-colored product was measured by spectrophotometry at a wavelength of 450 nm. Amount of SMN in test samples was determined using the calibration plot of optical density versus concentration of SMN in the standards.

Determination of Expression of SMN Target, Senataxin Protein (Functional Test)

Senataxin protein is a polyfunctional enzyme involved in the resolution of DNA-RNA structures called R-loops, which occur during transcription in case of absent or under-expressed SMN protein. The literature has reported a direct correlation between SMN and Senataxin expression levels, and indirect activation of Senataxin is one of the functions of SMN. In this regard, change in Senataxin expression was used as a functional test for SMN.

Senataxin expression level was determined by Western blot. Briefly, cells were lysed with RIPA buffer supplemented with protease inhibitor cocktail following experimental exposure (transfection, transduction, incubation), thereby obtaining protein lysate samples. The samples were applied onto a 10% polyacrylamide denaturing gel, thereafter the proteins were transferred onto PVDF membrane.

Membrane was incubated for 1 hour in 5% bovine serum albumin (BSA) solution in TBS-T buffer, thereafter the BSA solution was replaced with 1% BSA solution in TBS-T supplemented with primary antibodies specific for Senataxin. After 2 hours of incubation, the membrane was washed 3 times with 1% BSA solution in TBS-T and secondary antibody solution in TBS-T supplemented with 1% BSA was added. We used secondary antibodies conjugated with enzyme horseradish peroxidase.

Secondary antibodies were washed 3 times with 1% BSA solution in TBS-T, thereafter the protein signal was detected at the membrane using a chemiluminescence substrate and a gel imaging system. Resulting images were saved in digital format and the signal intensity was analyzed using the software of the gel imaging system.

The protein signal of the vinculin household gene was used as a control for normalization. Staining was carried out in a similar fashion.

Assembly and Purification of Viral Particles of AAV Recombinant Vectors

To assemble AAV particles containing the SMN1 gene or GFP control gene, we used HEK293 packaging cells, into which 3 plasmids were transfected using polyethylenimine as follows:

1. A plasmid comprising the AAV genome having a transgene expression cassette (SNMJ, GFP, SMN1+miR-23a or GFP+miR-23a);
2. A plasmid for expression of the AAV9 serotype Cap gene and the AAV2 serotype Rep gene. Each gene, using alternative reading frames, encodes several protein products;
3. A plasmid for expression of Ad5 (adenovirus serotype 5) genes that are required for assembly and packaging of AAV capsids.

After 72 hours, the cells were lysed and the viral particles were purified and concentrated using filtration and chromatography methods. The titer of the viral particles was determined by quantitative PCR with primers and a sample that were specific for the region of the recombinant viral genome and expressed as the copy number of viral genomes per 1 ml.

Transduction of Cell Cultures

U-87 cell line was inoculated similarly to transfection experiments, transfection with siRNA was carried out, following which the product with viral particles was added and, after 120 h, the cells were analyzed. Transduction efficiency was estimated by measuring the percentage of GFP+ cells.

The cultures being used were pre-tested with the check of the transduction efficiency. Briefly, the AAV9-GFP viral product was transduced into the cell lines in different ratios of cells and viral particles. The ratio of viral particle number to cell number is referred to as multiplicity of infection (MOI). The MOI of the AAV9-GFP virus ranged from 50,000 to 1,000,000. As a result, the optimal MOI of 400,000 was chosen for the U-87 line. Further U-87 transduction works were carried out at this MOI for all viruses.

Following transduction, gene and protein expression was analyzed as described above.

All samples were analyzed with 3 experimental replicates.

Injection of Viral Products into a Mouse Model of Spinal Muscular Atrophy (SMA)

Viral particles AAV9-SMN1, AAV9-GFP, AAV9-SMN1-miR-23a and AAV9-GFP-miR-23a were used for injection into SMA model mice. These mice do not express the mouse Smn gene, but have in the genome thereof one copy of the human SMN2 gene and one copy of the human SMN1 gene with exon 7 missing (SMN1Δ7). Without intervention or with a placebo injection, such mice are born, but poorly gain weight after birth and die after an average of 21 days.

Mice of the model line were genotyped on day 1 following birth, thereafter mice that contained no copy of the Smn gene were injected systemically (in the tail vein) with either a placebo (a solution that does not contain viral particles, but contains a buffer for dilution thereof), or one of the viruses at a dose of $3.2\times10^{14}$ vg/kg of body weight. Thereafter, the animals were kept under standard conditions and weighed daily, and survival curves were also plotted. 90 days following injection, survived animals were sacrificed for tissue analysis and the experiment was terminated.

Example 1. Assembly of Genetic Constructs Carrying Recombinant AAV Genome and Encoding SMN1, GFP and miR-23a Genes SMN1 gene sequence was produced by amplification with specific primers with cDNA synthesized based on total RNA of HEK293 cells, or assembled from a series of oligonucleotides (see above). During the amplification process, the Kozak sequence and ClaI restriction site were added from the 5'-end of the gene, and the XbaI restriction site was added from the 3'-end. The sequence of the SMN1 gene was thereafter cloned by the restriction-ligase method at the ClaI and XbaI sites into a commercial construct pAAV-GFP Control plasmid (VPK-402) from CellBiolab (USA), with substitution of the GFP gene with SMN1, thereby producing the pAAV-SMN1 construct.

An additional miR-23a expression cassette was inserted into the plasmids pAAV-GFP and pAAV-SMN1 that were produced previously. The additional miR-23a expression cassette consists of a promoter, a gene of interest (miR-23a, produced using PCR from genomic DNA of Huh7 cell line), and a polyadenylation signal. Target vectors were produced by linearizing at the PmlI site the recipient vectors (pAAV-GFP, pAAV-SMN1) followed by incorporation of the expression cassette with miR-23a at the cohesive ends.

The final vector contains all the necessary elements for expression and assembly of the gene as part of the recombinant AAV genome:

1. ITRs at the ends of the sequence that is encapsidated into a viral capsid;
2. A cassette for expression of the target gene (promoter, enhancer, intron, Kozak sequence, transgene, polyadenylation site);
3. If any, miR-23a expression cassette (promoter, miR-30-based microRNA cassette encoding miR-23a forward and reverse strands, polyadenylation signal);
4. The bacterial replication origin and antibiotic resistance gene to produce plasmid DNA in bacterial cells.

Example 2. Creating of Viral Products Expressing SMN1 and miR-23a

Plasmids pAAV-SMN1, pAAV-GFP, pAAV-SMN1-miR-23a, pAAV-GFP-miR-23a along with other plasmids required for producing recombinant AAV viral particles (see above) were used for the AAV production bioprocess. The serotype used was wild-type AAV9 or that having various mutations. In all cases, the properties of viral particles were compared only as long as the serotype used and capsid mutations, if any, were identical. All serotypes based on AAV9, either that of wild type or with mutations, are hereinafter referred to as AAV9 without specifying mutations.

Bioprocess resulted in recombinant viral particles designated as AAV9-SMN1, AAV9-GFP, AAV9-SMN1-miR-23a, AAV9-GFP-miR-23a. Following determining the titers of viral particles, all 3 products having the same MOI of 400,000 were used to transduce permissive cells, U-87, pre-transfected (24 hours before) with siRNA against SMN1 or siRNA having a non-specific sequence. Further analysis was performed only as long as the GFP transduction efficiency was at least 70%.

Following successful transduction, the cells were removed from the substrate, washed in a phosphate buffer, and the expression of SMN1 was analyzed at the mRNA and SMN protein levels as described above. It was shown that when transducing with viruses AAV9-SMN1 and AAV9-SMN1-miR-23a, SMN1 expression exceeded the endogenous mRNA level (Table 1, FIG. 1) and reconstituted to the endogenous level (observed in the control without SMN1-specific siRNA) at protein level (Table 2, FIG. 2).

TABLE 1

| Sample name | Mean mRNA copy number normalized to GAPDH copy number | Standard deviation |
|---|---|---|
| No siRNA, no virus | 0.00275 | 0.00021 |
| siNeg | 0.00168 | 0.00009 |
| siSMN1 | 0.0002 | 0.00002 |
| siNeg + AAV9-GFP | 0.00203 | 0.00033 |
| siSMN1 + AAV9-GFP | 0.00039 | 0.00006 |
| siNeg + AAV9-GFP-miR-23a | 0.00185 | 0.00028 |
| siSMN1 + AAV9-GFP-miR-23a | 0.00039 | 0.00001 |
| siNeg + AAV9-SMN1 | 0.10363 | 0.01045 |
| siSMN1 + AAV9-SMN1 | 0.33121 | 0.01495 |

TABLE 1-continued

| Sample name | Mean mRNA copy number normalized to GAPDH copy number | Standard deviation |
|---|---|---|
| siNeg + AAV9-SMN1-miR-23a | 0.24863 | 0.01715 |
| siSMN1 + AAV9-SMN1-miR-23a | 0.34258 | 0.0705 |

TABLE 2

| Sample name | Mean SMN amount (pg) normalized to total protein (μg) | Standard deviation |
|---|---|---|
| No siRNA, no virus | 83.37 | 8.58 |
| siNeg | 73.43 | 5.53 |
| siSMN1 | 5.45 | 1.36 |
| siNeg + AAV9-GFP | 67.95 | 12.41 |
| siSMN1 + AAV9-GFP | 5.4 | 1.02 |
| siNeg + AAV9-GFP-miR-23a | 71.82 | 3.16 |
| siSMN1 + AAV9-GFP-miR-23a | 4.8 | 1.23 |
| siNeg + AAV9-SMN1 | 116.4 | 1.85 |
| siSMN1 + AAV9-SMN1 | 69.15 | 5.71 |
| siNeg + AAV9-SMN1-miR-23a | 99.95 | 7.1 |
| siSMN1 + AAV9-SMN1-miR-23a | 91.13 | 4.93 |

Also, we determined miR-23a expression level in samples post-transduction. A significant excess of miR-23a expression was shown in samples transduced with viruses AAV9-SMN1-miR-23a, AAV9-GFP-miR-23a. In other samples, miR-23a expression did not differ from endogenous one. Transfection of siRNA against SMN1 did not affect miR-23a expression (Table 3, FIG. 3).

TABLE 3

| Sample name | Mean normalized amount of miR-23a (%) | Standard deviation |
|---|---|---|
| No siRNA, no virus | 100 | 12 |
| siNeg | 95 | 10 |
| siSMN1 | 113 | 13 |
| siNeg + AAV9-GFP | 124 | 12.41 |
| siSMN1 + AAV9-GFP | 107 | 11 |
| siNeg + AAV9-GFP-miR-23a | 843 | 33 |
| siSMN1 + AAV9-GFP-miR-23a | 768 | 26 |
| siNeg + AAV9-SMN1 | 116.4 | 16 |
| siSMN1 + AAV9-SMN1 | 77 | 8 |
| siNeg + AAV9-SMN1-miR-23a | 803 | 15 |
| siSMN1 + AAV9-SMN1-miR-23a | 920 | 19 |

It should be noted that changes in SMN1 expression with knockdown or reconstitution using the viral product did not affect miR-23a expression. Also, miR-23a overexpression had no effect on SMN1 expression.

Example 3. Functional Assessment of SMN1 and miR-23a In Vitro Post-Transduction The above design of experiment of SMN1 knockdown and reconstitution of expression thereof using transduction with viral particles was used to evaluate the functional cooperation of SMN1 and miR-23a in vitro. Among the many functions of SMN1, the protein is responsible for correct resolution of DNA-RNA duplexes that occur during transcription. Further, the main protein involved in resolution of duplexes is Senataxin, which, according to the literature, is indirectly activated by SMN. Thus, activation of Senataxin may be considered a functional test of SMN activity in cells.

Senataxin expression level in samples was determined by Western blot. It was found that with knockdown of SMN expression, Senataxin expression was decreased by about 2 times, and with reconstitution of SMN expression with virus AAV9-SMN1, it reconstituted to endogenous level. We observed a trend towards a slight increase in Senataxin expression in the case of SMN knockdown during transduction with control virus AAV9-GFP-miR-23a, but it was not statistically significant. It is important to note that in case of transduction with virus AAV9-SMN1-miR-23a, Senataxin expression was not only reconstituted to the endogenous level against the background of endogenous SMN knockdown, but also increased statistically significantly by 1.5-2 times (Table 4, FIG. 4).

TABLE 4

| Sample name | Mean normalized amount of Senataxin (%) | Standard deviation |
|---|---|---|
| No siRNA, no virus | 100 | 15 |
| siNeg | 109 | 17 |
| siSMN1 | 46 | 8 |
| siNeg + AAV9-GFP | 115 | 11 |
| siSMN1 + AAV9-GFP | 53 | 12 |
| siNeg + AAV9-GFP-miR-23a | 98 | 14 |
| siSMN1 + AAV9-GFP-miR-23a | 73 | 19 |
| siNeg + AAV9-SMN1 | 124 | 21 |
| siSMN1 + AAV9-SMN1 | 110 | 13 |
| siNeg + AAV9-SMN1-miR-23a | 196 | 17 |
| siSMN1 + AAV9-SMN1-miR-23a | 168 | 7 |

This confirms the synergistic effect of SMN and miR-23a on Senataxin expression, exceeding the effect of both miR-23a and SMN separately on the regulation of the gene.

Example 4. Synergistic Effect of SMN1 and miR-23a in Treating Animals of SMA Mouse Model Viral products AAV9-SMN1 and AAV9-SMN1-miR-23a were injected into the tail vein of SMA model mice on day 1 following birth at a dose of $3.6\times10^{14}$ vg/kg. We used a solution without viral particles (placebo) and a group of wild-type sibling mice that did not have the SMA phenotype due to their expression of Smn. Next, survival functions of mice in all groups were built. Upon reaching the point where it was possible to determine the median survival times for all groups, the medians were calculated.

The SMA phenotype was most corrected in the group injected with the virus AAV9-SMN1-miR-23a. Median survival time for the group was 55 days. This result was significantly different from the group injected with the virus AAV9-SMN1, where the median survival time was 21 days. For placebo-injected mice, the median was 16 days following birth (FIG. 5). This result shows the synergistic effect of SMN1 and miR-23a in treating SMA in an animal model of the disease.

The invention claimed is:

1. An isolated nucleic acid for producing a gene therapy viral product, said isolated nucleic acid comprising a nucleic acid that encodes a SMN1 protein (survival motor neuron protein) having the amino acid sequence of SEQ ID NO: 1, and a nucleic acid that encodes a microRNA miR-23a.

2. The isolated nucleic acid according to claim 1, wherein the nucleic acid that encodes the SMN1 protein having the amino acid sequence of SEQ ID NO: 1 comprises the nucleotide sequence of SEQ ID NO: 2.

3. The isolated nucleic acid according to claim 1, wherein the microRNA miR-23a has the nucleotide sequence of SEQ ID NO: 3.

4. The isolated nucleic acid according to claim 1, wherein the nucleic acid that encodes the microRNA miR-23a comprises the nucleotide sequence of SEQ ID NO: 4.

5. An expression cassette that comprises the nucleic acid according to claim 1.

6. The expression cassette according to claim 5, said expression cassette comprising the following elements in the 5'-end to 3'-end direction:

- a left-hand (first) ITR (inverted terminal repeats);
- a CMV (cytomegalovirus) enhancer;
- a CMV (cytomegalovirus) promoter;
- an intron of the hBG1 gene (hemoglobin subunit gamma 1 gene);
- a nucleic acid that encodes the SMN1 protein;
- an hGH1 polyadenylation signal (human growth hormone gene polyadenylation signal);
- an SV40 promoter (simian virus 40 promoter);
- a nucleic acid that encodes the microRNA miR-23a;
- an SV40 polyadenylation signal (simian virus 40 polyadenylation signal), and
- a right-hand (second) ITR.

7. The expression cassette according to claim 6, said expression cassette comprising a nucleic acid with SEQ ID NO: 6.

8. An expression vector that comprises the cassette according to claim 5.

9. An AAV9 (adeno-associated virus serotype 9)-based recombinant virus for the expression of the SMN1 gene in target cells, said AAV9-based recombinant virus comprising a capsid and the expression cassette according to claim 5, wherein the capsid comprises a AAV9 protein VP1.

10. The AAV9-based recombinant virus according to claim 9, wherein the capsid comprises the AAV9 protein VP1 having the amino acid sequence of SEQ ID NO: 7.

11. The AAV9-based recombinant virus according to claim 9, wherein the capsid includes the AAV9 protein VP1 having the amino acid sequence of SEQ ID NO: 7 with one or more point mutations.

12. The AAV9-based recombinant virus according to claim 9, wherein the capsid comprises the AAV9 protein VP1 having the amino acid sequence of SEQ ID NO: 7 or the amino acid sequence of SEQ ID NO: 7 with one or more point mutations, and the expression cassette comprises the following elements in the 5'-end to 3'-end direction:

- a left-hand (first) ITR (inverted terminal repeats);
- a CMV (cytomegalovirus) enhancer;
- a CMV (cytomegalovirus) promoter;
- an intron of the hBG1 gene (hemoglobin subunit gamma 1 gene);
- a nucleic acid that encodes the SMN1 protein;
- an hGH1 polyadenylation signal (human growth hormone gene polyadenylation signal);
- an SV40 promoter (simian virus 40 promoter);
- a nucleic acid that encodes the microRNA miR-23a;
- an SV40 polyadenylation signal (simian virus 40 polyadenylation signal), and
- a right-hand (second) ITR.

13. The AAV9-based recombinant virus according to claim 9, wherein the capsid comprises the AAV9 protein VP1 having the amino acid sequence of SEQ ID NO: 7 or the amino acid sequence of SEQ ID NO: 7 with one or more point mutations, and the expression cassette comprises a nucleic acid with SEQ ID NO: 6.

14. A pharmaceutical composition for delivering the SMN1 gene to target cells, said pharmaceutical composition comprising the AAV9-based recombinant virus according to claim 9 in combination with one or more pharmaceutically acceptable excipients.

15. A method for modulating motor function in a subject having a motor neuron disorder, said method comprising administering a therapeutically effective amount of the AAV9-based recombinant virus according to claim 9 into the cells of the subject.

16. A method for providing the SMN protein to a subject having spinal muscular atrophy, said method comprising administering a therapeutically effective amount of the AAV9-based recombinant virus according to claim 9 into the cells of the subject in need thereof.

17. A method for delivering the SMN1 gene to the target cells of a subject having spinal muscular atrophy, said method comprising administering the AAV9-based recombinant virus according to claim 9 into the cells of the subject.

18. A method for treating spinal muscular atrophy in a subject, said method comprising administering a therapeutically effective amount of the AAV9-based recombinant virus according to claim 9 to a subject having spinal muscular atrophy.

* * * * *

SEQUENCE LISTING

```
<160> NUMBER OF SEQ ID NOS: 17

<210> SEQ ID NO 1
<211> LENGTH: 294
<212> TYPE: PRT
<213> ORGANISM: Unknown
<220> FEATURE:
<223> OTHER INFORMATION: Amino acid sequence of SMN1 protein

<400> SEQUENCE: 1

Met Ala Met Ser Ser Gly Gly Ser Gly Gly Gly Val Pro Glu Gln Glu
1               5                   10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110

Ile Ala Ser Ile Asp Phe Lys Arg Glu Thr Cys Val Val Val Tyr Thr
        115                 120                 125

Gly Tyr Gly Asn Arg Glu Glu Gln Asn Leu Ser Asp Leu Leu Ser Pro
    130                 135                 140

Ile Cys Glu Val Ala Asn Asn Ile Glu Gln Asn Ala Gln Glu Asn Glu
```

145 150 155 160

Asn Glu Ser Gln Val Ser Thr Asp Glu Ser Glu Asn Ser Arg Ser Pro
165 170 175

Gly Asn Lys Ser Asp Asn Ile Lys Pro Lys Ser Ala Pro Trp Asn Ser
180 185 190

Phe Leu Pro Pro Pro Pro Pro Met Pro Gly Pro Arg Leu Gly Pro Gly
195 200 205

Lys Pro Gly Leu Lys Phe Asn Gly Pro Pro Pro Pro Pro Pro Pro Pro
210 215 220

Pro Pro His Leu Leu Ser Cys Trp Leu Pro Pro Phe Pro Ser Gly Pro
225 230 235 240

Pro Ile Ile Pro Pro Pro Pro Pro Ile Cys Pro Asp Ser Leu Asp Asp
245 250 255

Ala Asp Ala Leu Gly Ser Met Leu Ile Ser Trp Tyr Met Ser Gly Tyr
260 265 270

His Thr Gly Tyr Tyr Met Gly Phe Arg Gln Asn Gln Lys Glu Gly Arg
275 280 285

Cys Ser His Ser Leu Asn
290

<210> SEQ ID NO 2
<211> LENGTH: 882
<212> TYPE: DNA
<213> ORGANISM: Artificial Sequence
<220> FEATURE:
<223> OTHER INFORMATION: Nucleic acid sequence encoding SMN1 protein

<400> SEQUENCE: 2
atggccatga gcagcggcgg cagcggcggc ggcgtgcctg agcaagagga cagcgtgctg 60
ttcagaagag gcaccggcca gagcgacgac agcgacatct gggacgacac cgccctgatc 120
aaggcctacg acaaggccgt ggccagcttc aagcacgccc tgaagaacgg cgacatctgc 180
gagaccagcg gcaagcccaa gaccaccccc aagagaaagc ccgccaagaa gaacaagagc 240
cagaagaaga acaccgccgc cagcctgcag cagtggaagg tgggcgacaa gtgcagcgcc 300
atctggagcg aggacggctg catctacccc gccaccatcg ccagcatcga cttcaagaga 360
gagacctgcg tggtggtgta caccggctac ggcaacagag aggagcagaa cctgagcgac 420
ctgctgagcc ccatctgcga ggtggccaac aacatcgagc agaacgccca agagaacgag 480
aacgagagcc aagtgagcac cgacgagagc gagaacagca gaagccccgg caacaagagc 540
gacaacatca agcccaagag cgccccctgg aacagcttcc tgccccctcc ccccccctatg 600 cccggcccta gactgggccc tggcaagcct ggcctgaagt tcaacggccc cccccccccct 660 cctcctcctc ctcctcctca cctgctgagc tgctggctgc ccccccttccc cagcggccct 720 cctatcatcc ctcctccccc ccccatctgc cccgacagcc tggacgacgc cgacgccctg 780
ggcagcatgc tgatcagctg gtacatgagc ggctaccaca ccggctacta catgggcttc 840
agacagaacc agaaggaggg ccggtgcagc cacagcctga ac 882

<210> SEQ ID NO 3
<211> LENGTH: 73
<212> TYPE: RNA
<213> ORGANISM: Artificial Sequence
<220> FEATURE:
<223> OTHER INFORMATION: microRNA miR-23a

<400> SEQUENCE: 3
ggccggcugg gguuccuggg gaugggauuu gcuuccuguc acaaaucaca uugccaggga 60
uuuccaaccg acc 73

<210> SEQ ID NO 4
<211> LENGTH: 648
<212> TYPE: DNA
<213> ORGANISM: Artificial Sequence
<220> FEATURE:
<223> OTHER INFORMATION: Nucleic acid sequence encoding microRNA miR-23a
(prior to processing)

<400> SEQUENCE: 4
catgcaagtt gctgtagcct ccttgtcccg catgggccct ctaggtatct ctgcctctcc 60
agtcctgggg ctggaacgga gggcacagct aggctccagc tccccgtgtg gtggctcctg 120
catatgagaa aagagcttcc ctgtgatcaa aggaagcatc tggggacctg gaggggaggt 180
gtccccaaat ctcattacct cctttgctct ctctctcttt ctcccctcca ggtgccagcc 240
tctggccccg cccggtgccc ccctcacccc tgtgccacgg ccggctgggg ttcctgggga 300
tgggatttgc ttcctgtcac aaatcacatt gccagggatt tccaaccgac cctgagctct 360
gccaccgagg atgctgcccg gggacggggt ggcagagagg ccccgaagcc tgtgcctggc 420
ctgaggagca gggcttagct gcttgtgagc agggtccaca ccaagtcgtg ttcacagtgg 480
ctaagttccg ccccccaggc cctcacctcc tctggccttg ccgcctgtcc cctgctgccg 540
cctgtctgcc tgccatcctg ctgcctggcc tccctgggct ctgcctcccg tgcctactga 600
gctgaaacac agttggtttg tgtacactgg ctcagttcag caggaaca 648

<210> SEQ ID NO 5
<211> LENGTH: 73
<212> TYPE: DNA
<213> ORGANISM: Artificial Sequence
<220> FEATURE:
<223> OTHER INFORMATION: Nucleic acid sequence encoding microRNA miR-23a
(following processing)

<400> SEQUENCE: 5
ggccggctgg ggttcctggg gatgggattt gcttcctgtc acaaatcaca ttgccaggga 60
tttccaaccg acc 73

<210> SEQ ID NO 6
<211> LENGTH: 3972
<212> TYPE: DNA
<213> ORGANISM: Artificial Sequence
<220> FEATURE:
<223> OTHER INFORMATION: Nucleic acid sequence of the expression
cassette (complete)

<400> SEQUENCE: 6
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtctagtt attaatagta atcaattacg gggtcattag 180
ttcatagccc atatatggag ttccgcgtta cataacttac ggtaaatggc ccgcctggct 240
gaccgcccaa cgacccccgc ccattgacgt caataatgac gtatgttccc atagtaacgc 300
caatagggac tttccattga cgtcaatggg tggagtattt acggtaaact gcccacttgg 360
cagtacatca agtgtatcat atgccaagta cgccccctat tgacgtcaat gacggtaaat 420
ggcccgcctg gcattatgcc cagtacatga ccttatggga ctttcctact tggcagtaca 480

```
tctacgtatt agtcatcgct attaccatgg tgatgcggtt ttggcagtac atcaatgggc    540
gtggatagcg gtttgactca cggggatttc caagtctcca ccccattgac gtcaatggga    600
gtttgttttg gcaccaaaat caacgggact ttccaaaatg tcgtaacaac tccgccccat    660
tgacgcaaat gggcggtagg cgtgtacggt gggaggtcta tataagcaga gctcgtttag    720
tgaaccgtca gatcgcctgg agacgccatc cacgctgttt tgacctccat agaagacacc    780
gggaccgatc cagcctccgc ggattcgaat cccggccggg aacggtgcat tggaacgcgg    840
attccccgtg ccaagagtga cgtaagtacc gcctatagag tctataggcc cacaaaaaat    900
gctttcttct tttaatatac ttttttgttt atcttatttc taatactttc cctaatctct    960
ttctttcagg gcaataatga tacaatgtat catgcctctt tgcaccattc taaagaataa   1020
cagtgataat ttctgggtta aggcaatagc aatatttctg catataaata tttctgcata   1080
taaattgtaa ctgatgtaag aggtttcata ttgctaatag cagctacaat ccagctacca   1140
ttctgctttt attttatggt tgggataagg ctggattatt ctgagtccaa gctaggccct   1200
tttgctaatc atgttcatac ctcttatctt cctcccacag ctcctgggca acgtgctggt   1260
ctgtgtgctg gcccatcact ttggcaaaga attgggattc gaacatcgat tgtaattcat   1320
gagccaccat ggccatgagc agcggcggca gcggcggcgg cgtgcctgag caagaggaca   1380
gcgtgctgtt cagaagaggc accggccaga gcgacgacag cgacatctgg gacgacaccg   1440
ccctgatcaa ggcctacgac aaggccgtgg ccagcttcaa gcacgccctg aagaacggcg   1500
acatctgcga gaccagcggc aagcccaaga ccacccccaa gagaaagccc gccaagaaga   1560
acaagagcca gaagaagaac accgccgcca gcctgcagca gtggaaggtg ggcgacaagt   1620
gcagcgccat ctggagcgag gacggctgca tctaccccgc caccatcgcc agcatcgact   1680
tcaagagaga gacctgcgtg gtggtgtaca ccggctacgg caacagagag gagcagaacc   1740
tgagcgacct gctgagcccc atctgcgagg tggccaacaa catcgagcag aacgcccaag   1800
agaacgagaa cgagagccaa gtgagcaccg acgagagcga gaacagcaga agccccggca   1860
acaagagcga caacatcaag cccaagagcg ccccctggaa cagcttcctg ccccctcccc   1920
cccctatgcc cggccctaga ctgggccctg gcaagcctgg cctgaagttc aacggccccc   1980
ccccccctcc tcctcctcct cctcctcacc tgctgagctg ctggctgccc cccttcccca   2040
gcggccctcc tatcatccct cctccccccc ccatctgccc cgacagcctg gacgacgccg   2100
acgccctggg cagcatgctg atcagctggt acatgagcgg ctaccacacc ggctactaca   2160
tgggcttcag acagaaccag aaggagggcc ggtgcagcca cagcctgaac tgatctagag   2220
tcgacctgca gaagcttgcc tcgagcagcg ctgctcgaga gatctacggg tggcatccct   2280
gtgacccctc cccagtgcct ctcctggccc tggaagttgc cactccagtg cccaccagcc   2340
ttgtcctaat aaaattaagt tgcatcattt tgtctgacta ggtgtccttc tataatatta   2400
tggggtggag gggggtggta tggagcaagg ggcaagttgg gaagacaacc tgtagggcct   2460
gcggggtcta ttgggaacca agctggagtg cagtggcaca atcttggctc actgcaatct   2520
ccgcctcctg ggttcaagcg attctcctgc ctcagcctcc cgagttgttg ggattccagg   2580
catgcatgac caggctcagc taatttttgt ttttttggta gagacggggt ttcaccatat   2640
tggccaggct ggtctccaac tcctaatctc aggtgatcta cccaccttgg cctcccaaat   2700
tgctgggatt acaggcgtga accactgctc ccttccctgt ccttctgatt ttgtaggtaa   2760
ccactagaga aatgttctgg cacctgcact tgcactgggg acagcctatt ttgctagttt   2820
gttttgtttc gttttgtttt gatggagagc gtatgttagt actatcgatt cacacaaaaa   2880
```

```
accaacacac agatgtaatg aaaataaaga tattttattg cggccgctgt tcctgctgaa   2940

ctgagccagt gtacacaaac caactgtgtt tcagctcagt aggcacggga ggcagagccc   3000

agggaggcca ggcagcagga tggcaggcag acaggcggca gcaggggaca ggcggcaagg   3060

ccagaggagg tgagggcctg gggggcggaa cttagccact gtgaacacga cttggtgtgg   3120

accctgctca caagcagcta agccctgctc ctcaggccag gcacaggctt cggggcctct   3180

ctgccacccc gtccccgggc agcatcctcg gtggcagagc tcagggtcgg ttggaaatcc   3240

ctggcaatgt gatttgtgac aggaagcaaa tcccatcccc aggaacccca gccggccgtg   3300

gcacaggggt gagggggca ccgggcgggg ccagaggctg gcacctggag gggagaaaga   3360

gagagagagc aaaggaggta atgagatttg gggacacctc ccctccaggt ccccagatgc   3420

ttcctttgat cacagggaag ctcttttctc atatgcagga gccaccacac ggggagctgg   3480

agcctagctg tgccctccgt tccagcccca ggactggaga ggcagagata cctagagggc   3540

ccatgcggga caaggaggct acagcaactt gcatggccgc agctttttgc aaaagcctag   3600

gcctccaaaa aagcctcctc actacttctg gaatagctca gaggccgagg cggcctcggc   3660

ctctgcataa ataaaaaaaa ttagtcagcg atggggcgga gaatgggcgg aactgggcgg   3720

agttaggggc gggatgggcg gagttagggg cgggactatg gttgctgact aattgagatg   3780

cagggccgct ccaagtacct cccgtacctt aagtgcggac cgagcggccg caggaacccc   3840

tagtgatgga gttggccact ccctctctgc gcgctcgctc gctcactgag gccgggcgac   3900

caaaggtcgc ccgacgcccg ggctttgccc gggcggcctc agtgagcgag cgagcgcgca   3960

gctgcctgca gg                                                       3972


<210> SEQ ID NO 7
<211> LENGTH: 736
<212> TYPE: PRT
<213> ORGANISM: Unknown
<220> FEATURE:
<223> OTHER INFORMATION: Amino acid sequence of AAV9 protein VP1

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160
```

-continued

```
Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
```

```
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 8
<211> LENGTH: 599
<212> TYPE: PRT
<213> ORGANISM: Unknown
<220> FEATURE:
<223> OTHER INFORMATION: Amino acid sequence of AAV9 protein VP2

<400> SEQUENCE: 8

Thr Ala Pro Gly Lys Lys Arg Pro Val Glu Gln Ser Pro Gln Glu Pro
1               5                   10                  15

Asp Ser Ser Ala Gly Ile Gly Lys Ser Gly Ala Gln Pro Ala Lys Lys
            20                  25                  30

Arg Leu Asn Phe Gly Gln Thr Gly Asp Thr Glu Ser Val Pro Asp Pro
        35                  40                  45

Gln Pro Ile Gly Glu Pro Pro Ala Ala Pro Ser Gly Val Gly Ser Leu
    50                  55                  60

Thr Met Ala Ser Gly Gly Gly Ala Pro Val Ala Asp Asn Asn Glu Gly
65                  70                  75                  80

Ala Asp Gly Val Gly Ser Ser Ser Gly Asn Trp His Cys Asp Ser Gln
                85                  90                  95

Trp Leu Gly Asp Arg Val Ile Thr Thr Ser Thr Arg Thr Trp Ala Leu
            100                 105                 110

Pro Thr Tyr Asn Asn His Leu Tyr Lys Gln Ile Ser Asn Ser Thr Ser
        115                 120                 125

Gly Gly Ser Ser Asn Asp Asn Ala Tyr Phe Gly Tyr Ser Thr Pro Trp
    130                 135                 140

Gly Tyr Phe Asp Phe Asn Arg Phe His Cys His Phe Ser Pro Arg Asp
145                 150                 155                 160

Trp Gln Arg Leu Ile Asn Asn Asn Trp Gly Phe Arg Pro Lys Arg Leu
                165                 170                 175

Asn Phe Lys Leu Phe Asn Ile Gln Val Lys Glu Val Thr Asp Asn Asn
            180                 185                 190

Gly Val Lys Thr Ile Ala Asn Asn Leu Thr Ser Thr Val Gln Val Phe
        195                 200                 205

Thr Asp Ser Asp Tyr Gln Leu Pro Tyr Val Leu Gly Ser Ala His Glu
```

```
    210                 215                 220

Gly Cys Leu Pro Pro Phe Pro Ala Asp Val Phe Met Ile Pro Gln Tyr
225                 230                 235                 240

Gly Tyr Leu Thr Leu Asn Asp Gly Ser Gln Ala Val Gly Arg Ser Ser
                245                 250                 255

Phe Tyr Cys Leu Glu Tyr Phe Pro Ser Gln Met Leu Arg Thr Gly Asn
            260                 265                 270

Asn Phe Gln Phe Ser Tyr Glu Phe Glu Asn Val Pro Phe His Ser Ser
        275                 280                 285

Tyr Ala His Ser Gln Ser Leu Asp Arg Leu Met Asn Pro Leu Ile Asp
    290                 295                 300

Gln Tyr Leu Tyr Tyr Leu Ser Lys Thr Ile Asn Gly Ser Gly Gln Asn
305                 310                 315                 320

Gln Gln Thr Leu Lys Phe Ser Val Ala Gly Pro Ser Asn Met Ala Val
                325                 330                 335

Gln Gly Arg Asn Tyr Ile Pro Gly Pro Ser Tyr Arg Gln Gln Arg Val
            340                 345                 350

Ser Thr Thr Val Thr Gln Asn Asn Asn Ser Glu Phe Ala Trp Pro Gly
        355                 360                 365

Ala Ser Ser Trp Ala Leu Asn Gly Arg Asn Ser Leu Met Asn Pro Gly
    370                 375                 380

Pro Ala Met Ala Ser His Lys Glu Gly Glu Asp Arg Phe Phe Pro Leu
385                 390                 395                 400

Ser Gly Ser Leu Ile Phe Gly Lys Gln Gly Thr Gly Arg Asp Asn Val
                405                 410                 415

Asp Ala Asp Lys Val Met Ile Thr Asn Glu Glu Glu Ile Lys Thr Thr
            420                 425                 430

Asn Pro Val Ala Thr Glu Ser Tyr Gly Gln Val Ala Thr Asn His Gln
        435                 440                 445

Ser Ala Gln Ala Gln Ala Gln Thr Gly Trp Val Gln Asn Gln Gly Ile
    450                 455                 460

Leu Pro Gly Met Val Trp Gln Asp Arg Asp Val Tyr Leu Gln Gly Pro
465                 470                 475                 480

Ile Trp Ala Lys Ile Pro His Thr Asp Gly Asn Phe His Pro Ser Pro
                485                 490                 495

Leu Met Gly Gly Phe Gly Met Lys His Pro Pro Pro Gln Ile Leu Ile
            500                 505                 510

Lys Asn Thr Pro Val Pro Ala Asp Pro Pro Thr Ala Phe Asn Lys Asp
        515                 520                 525

Lys Leu Asn Ser Phe Ile Thr Gln Tyr Ser Thr Gly Gln Val Ser Val
    530                 535                 540

Glu Ile Glu Trp Glu Leu Gln Lys Glu Asn Ser Lys Arg Trp Asn Pro
545                 550                 555                 560

Glu Ile Gln Tyr Thr Ser Asn Tyr Tyr Lys Ser Asn Asn Val Glu Phe
                565                 570                 575

Ala Val Asn Thr Glu Gly Val Tyr Ser Glu Pro Arg Pro Ile Gly Thr
            580                 585                 590

Arg Tyr Leu Thr Arg Asn Leu
        595
```

<210> SEQ ID NO 9
<211> LENGTH: 534
<212> TYPE: PRT
<213> ORGANISM: Unknown

<220> FEATURE:
<223> OTHER INFORMATION: Amino acid sequence of AAV9 protein VP3

<400> SEQUENCE: 9

```
Met Ala Ser Gly Gly Gly Ala Pro Val Ala Asp Asn Asn Glu Gly Ala
1               5                   10                  15

Asp Gly Val Gly Ser Ser Ser Gly Asn Trp His Cys Asp Ser Gln Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Asn Ser Thr Ser Gly
    50                  55                  60

Gly Ser Ser Asn Asp Asn Ala Tyr Phe Gly Tyr Ser Thr Pro Trp Gly
65                  70                  75                  80

Tyr Phe Asp Phe Asn Arg Phe His Cys His Phe Ser Pro Arg Asp Trp
                85                  90                  95

Gln Arg Leu Ile Asn Asn Asn Trp Gly Phe Arg Pro Lys Arg Leu Asn
            100                 105                 110

Phe Lys Leu Phe Asn Ile Gln Val Lys Glu Val Thr Asp Asn Asn Gly
        115                 120                 125

Val Lys Thr Ile Ala Asn Asn Leu Thr Ser Thr Val Gln Val Phe Thr
    130                 135                 140

Asp Ser Asp Tyr Gln Leu Pro Tyr Val Leu Gly Ser Ala His Glu Gly
145                 150                 155                 160

Cys Leu Pro Pro Phe Pro Ala Asp Val Phe Met Ile Pro Gln Tyr Gly
                165                 170                 175

Tyr Leu Thr Leu Asn Asp Gly Ser Gln Ala Val Gly Arg Ser Ser Phe
            180                 185                 190

Tyr Cys Leu Glu Tyr Phe Pro Ser Gln Met Leu Arg Thr Gly Asn Asn
        195                 200                 205

Phe Gln Phe Ser Tyr Glu Phe Glu Asn Val Pro Phe His Ser Ser Tyr
    210                 215                 220

Ala His Ser Gln Ser Leu Asp Arg Leu Met Asn Pro Leu Ile Asp Gln
225                 230                 235                 240

Tyr Leu Tyr Tyr Leu Ser Lys Thr Ile Asn Gly Ser Gly Gln Asn Gln
                245                 250                 255

Gln Thr Leu Lys Phe Ser Val Ala Gly Pro Ser Asn Met Ala Val Gln
            260                 265                 270

Gly Arg Asn Tyr Ile Pro Gly Pro Ser Tyr Arg Gln Gln Arg Val Ser
        275                 280                 285

Thr Thr Val Thr Gln Asn Asn Asn Ser Glu Phe Ala Trp Pro Gly Ala
    290                 295                 300

Ser Ser Trp Ala Leu Asn Gly Arg Asn Ser Leu Met Asn Pro Gly Pro
305                 310                 315                 320

Ala Met Ala Ser His Lys Glu Gly Glu Asp Arg Phe Phe Pro Leu Ser
                325                 330                 335

Gly Ser Leu Ile Phe Gly Lys Gln Gly Thr Gly Arg Asp Asn Val Asp
            340                 345                 350

Ala Asp Lys Val Met Ile Thr Asn Glu Glu Glu Ile Lys Thr Thr Asn
        355                 360                 365

Pro Val Ala Thr Glu Ser Tyr Gly Gln Val Ala Thr Asn His Gln Ser
    370                 375                 380

Ala Gln Ala Gln Ala Gln Thr Gly Trp Val Gln Asn Gln Gly Ile Leu
385                 390                 395                 400
```

```
Pro Gly Met Val Trp Gln Asp Arg Asp Val Tyr Leu Gln Gly Pro Ile
                405                 410                 415

Trp Ala Lys Ile Pro His Thr Asp Gly Asn Phe His Pro Ser Pro Leu
            420                 425                 430

Met Gly Gly Phe Gly Met Lys His Pro Pro Pro Gln Ile Leu Ile Lys
        435                 440                 445

Asn Thr Pro Val Pro Ala Asp Pro Pro Thr Ala Phe Asn Lys Asp Lys
    450                 455                 460

Leu Asn Ser Phe Ile Thr Gln Tyr Ser Thr Gly Gln Val Ser Val Glu
465                 470                 475                 480

Ile Glu Trp Glu Leu Gln Lys Glu Asn Ser Lys Arg Trp Asn Pro Glu
                485                 490                 495

Ile Gln Tyr Thr Ser Asn Tyr Tyr Lys Ser Asn Asn Val Glu Phe Ala
            500                 505                 510

Val Asn Thr Glu Gly Val Tyr Ser Glu Pro Arg Pro Ile Gly Thr Arg
        515                 520                 525

Tyr Leu Thr Arg Asn Leu
    530


<210> SEQ ID NO 10
<211> LENGTH: 130
<212> TYPE: DNA
<213> ORGANISM: Unknown
<220> FEATURE:
<223> OTHER INFORMATION: left-hand (first) ITR (inverted terminal
      repeats)

<400> SEQUENCE: 10

cctgcaggca gctgcgcgct cgctcgctca ctgaggccgc ccgggcgtcg ggcgaccttt      60

ggtcgcccgg cctcagtgag cgagcgagcg cgcagagagg gagtggccaa ctccatcact     120

aggggttcct                                                            130


<210> SEQ ID NO 11
<211> LENGTH: 304
<212> TYPE: DNA
<213> ORGANISM: Unknown
<220> FEATURE:
<223> OTHER INFORMATION: CMV (Cytomegalovirus) enhancer

<400> SEQUENCE: 11

cgttacataa cttacggtaa atggcccgcc tggctgaccg cccaacgacc cccgcccatt      60

gacgtcaata atgacgtatg ttcccatagt aacgccaata gggactttcc attgacgtca     120

atgggtggag tatttacggt aaactgccca cttggcagta catcaagtgt atcatatgcc     180

aagtacgccc cctattgacg tcaatgacgg taaatggccc gcctggcatt atgcccagta     240

catgacctta tgggactttc ctacttggca gtacatctac gtattagtca tcgctattac     300

catg                                                                  304


<210> SEQ ID NO 12
<211> LENGTH: 204
<212> TYPE: DNA
<213> ORGANISM: Unknown
<220> FEATURE:
<223> OTHER INFORMATION: CMV (Cytomegalovirus) promoter

<400> SEQUENCE: 12

gtgatgcggt tttggcagta catcaatggg cgtggatagc ggtttgactc acggggattt      60
```

ccaagtctcc accccattga cgtcaatggg agtttgtttt ggcaccaaaa tcaacgggac 120
tttccaaaat gtcgtaacaa ctccgcccca ttgacgcaaa tgggcggtag gcgtgtacgg 180
tgggaggtct atataagcag agct 204

<210> SEQ ID NO 13
<211> LENGTH: 493
<212> TYPE: DNA
<213> ORGANISM: Unknown
<220> FEATURE:
<223> OTHER INFORMATION: intron of hBG1 gene (hemoglobin subunit gamma 1)

<400> SEQUENCE: 13
cgaatcccgg ccgggaacgg tgcattggaa cgcggattcc ccgtgccaag agtgacgtaa 60
gtaccgccta tagagtctat aggcccacaa aaaatgcttt cttcttttaa tatacttttt 120
tgtttatctt atttctaata ctttccctaa tctctttctt tcagggcaat aatgatacaa 180
tgtatcatgc ctctttgcac cattctaaag aataacagtg ataatttctg ggttaaggca 240
atagcaatat ttctgcatat aaatatttct gcatataaat tgtaactgat gtaagaggtt 300
tcatattgct aatagcagct acaatccagc taccattctg cttttatttt atggttggga 360
taaggctgga ttattctgag tccaagctag gcccttttgc taatcatgtt catacctctt 420
atcttcctcc cacagctcct gggcaacgtg ctggtctgtg tgctggccca tcactttggc 480
aaagaattgg gat 493

<210> SEQ ID NO 14
<211> LENGTH: 479
<212> TYPE: DNA
<213> ORGANISM: Unknown
<220> FEATURE:
<223> OTHER INFORMATION: polyadenylation signal of hGH1 (polyadenylation signal (poly(A)) of human growth hormone)

<400> SEQUENCE: 14
acgggtggca tccctgtgac ccctccccag tgcctctcct ggccctggaa gttgccactc 60
cagtgcccac cagccttgtc ctaataaaat taagttgcat cattttgtct gactaggtgt 120
ccttctataa tattatgggg tggagggggg tggtatggag caaggggcaa gttgggaaga 180
caacctgtag ggcctgcggg gtctattggg aaccaagctg gagtgcagtg gcacaatctt 240
ggctcactgc aatctccgcc tcctgggttc aagcgattct cctgcctcag cctcccgagt 300
tgttgggatt ccaggcatgc atgaccaggc tcagctaatt tttgtttttt tggtagagac 360
ggggtttcac catattggcc aggctggtct ccaactccta atctcaggtg atctacccac 420
cttggcctcc caaattgctg ggattacagg cgtgaaccac tgctcccttc cctgtcctt 479

<210> SEQ ID NO 15
<211> LENGTH: 202
<212> TYPE: DNA
<213> ORGANISM: Unknown
<220> FEATURE:
<223> OTHER INFORMATION: SV40 promoter (simian virus 40 promoter)

<400> SEQUENCE: 15
tgcatctcaa ttagtcagca accatagtcc cgcccctaac tccgcccatc ccgcccctaa 60
ctccgcccag ttccgcccat tctccgcccc atcgctgact aatttttttt atttatgcag 120
aggccgaggc cgcctcggcc tctgagctat tccagaagta gtgaggaggc ttttttggag 180
gcctaggctt ttgcaaaaag ct 202

```
<210> SEQ ID NO 16
<211> LENGTH: 154
<212> TYPE: DNA
<213> ORGANISM: Unknown
<220> FEATURE:
<223> OTHER INFORMATION: SV40 polyadenylation signal (simian virus 40
      polyadenylation signal)

<400> SEQUENCE: 16

aataaaatat ctttattttc attacatctg tgtgttggtt ttttgtgtga atcgatagta     60

ctaacatacg ctctccatca aaacaaaacg aaacaaaaca aactagcaaa ataggctgtc    120

cccagtgcaa gtgcaggtgc cagaacattt ctct                                154


<210> SEQ ID NO 17
<211> LENGTH: 141
<212> TYPE: DNA
<213> ORGANISM: Unknown
<220> FEATURE:
<223> OTHER INFORMATION: right-hand (second) ITR

<400> SEQUENCE: 17

aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag ctgcctgcag g                                              141
```